United States Patent [19]
Suzuki et al.

[11] Patent Number: 5,856,479
[45] Date of Patent: Jan. 5, 1999

[54] FLUORESCENT GROUP-CONTAINING CARBODIIMIDE COMPOUND

[75] Inventors: Osamu Suzuki; Gen Masuda; Namiko Shiohata; Kazuko Matsumoto, all of Tokyo, Japan

[73] Assignee: Nisshinbo Industries, Inc., Tokyo, Japan

[21] Appl. No.: 857,536

[22] Filed: May 16, 1997

[30]   Foreign Application Priority Data

May 20, 1996  [JP]  Japan ..................................... 8-124793
Nov. 8, 1996  [JP]  Japan ..................................... 8-296887
Feb. 17, 1997 [JP]  Japan ..................................... 9-032459

[51] Int. Cl.$^6$ ........................... C07C 267/00; C12Q 1/68
[52] U.S. Cl. ........................ 544/151; 546/176; 548/110; 548/126; 548/169; 549/284; 534/15; 564/86; 564/196; 564/252
[58] Field of Search ..................... 564/252, 196, 564/86; 544/151; 549/284; 546/176; 534/15; 548/169, 110, 126

[56]   References Cited

U.S. PATENT DOCUMENTS

| | | | |
|---|---|---|---|
| 4,024,178 | 5/1977 | Landucci et al. ................... | 564/252 X |
| 4,895,955 | 1/1990 | Ford et al. .............................. | 548/303 |
| 5,105,010 | 4/1992 | Sundararaman et al. ............... | 564/252 |
| 5,117,059 | 5/1992 | Tylor ...................................... | 564/252 |

FOREIGN PATENT DOCUMENTS 0 718 300 A1   6/1996   European Pat. Off. .

OTHER PUBLICATIONS

Chemical Abstracts Service, vol. 124, No. 15, Apr. 8, 1996 Masuda et al, #197627C. Yamamoto, JP 06271581, Sep. 27, 1994 (Abstract).

*Primary Examiner*—Floyd D. Higel
*Attorney, Agent, or Firm*—Jones & Askew

[57]   ABSTRACT

Using the fluorescent group-containing carbodiimide compound represented-by the following formula (I) as the label and the like in the nucleic acid detection method, immunoassay, or chemiluminescence assay, labeling can be made efficiently for a short time, a nucleic acid derived from nature can be labelled, and highly sensitive assay is enabled.

$$B-Y^3-N=C=N-Y^2-W-Y^1-[A]_n-F \qquad (I)$$

wherein F represents a fluorescent group;

A represents a moiety selected from the group consisting of $-CH_2-$, $-NHCO-$, $-CONH-$, $-O-$, $-S-$, $-NR-$ wherein R is an alkyl group, $-COO-$, $-OCO-$, $-NHSO_2-$, and $-SO_2NH-$;

n is 0 or 1;

W represents a direct bond or a quaternary ammonium group;

$Y^1$, $Y^2$ and $Y^3$ each represents an alkylene group which may have a functional group in its main chain; and B represents H or a monovalent organic group which may be the same as or different from that represented by $-W-Y^1-[A]_n-F$.

9 Claims, No Drawings

FLUORESCENT GROUP-CONTAINING CARBODIIMIDE COMPOUND

FIELD OF THE INVENTION

The present invention relates to a novel fluorescent group-containing carbodiimide compound. More specifically, the present invention relates to a novel fluorescent group-containing carbodiimide compound which is an assay reagent having high sensitivity and capable of labeling easily, a process for producing it, and an assay method using it.

BACKGROUND OF THE INVENTION

In various biological analyses, assay methods for detecting a target substance using a specific detectable label have been developed so far. For example, in the nucleic acid detection method by hybridization using the labelled nucleic acid, a nucleic acid (DNA or RNA) to be used as a probe is labelled and brought into contact with a sample containing a nucleic acid to be detected under conditions that hybrid can be formed. If the sample contains a nucleic acid having a base sequence complementary to that of the nucleic acid used as a probe, this nucleic acid binds (hybridize) to the probe to form a nucleic acid-nucleic acid hybrid. The target nucleic acid can be detected by measuring the label contained in the hybrid. In the immunoassay using labelled antigen or a labelled antibody, when an antigen is to be detected, it can be detected by labeling an antibody which is specifically bound to the antigen, effecting formation of an antigen-antibody complex, and detecting the label contained in the complex.

As the label to be used in such nucleic acid detection methods and immunoassay, radioactive substances, non-radioactive substances such as biotin or digoxigenin compounds, fluorescent substances, and the like are exemplified.

The following methods are known as the methods of introducing a fluorescent substance into, for example, a nucleic acid: the method of introducing a fluorescent substance-bound nucleotide into a nucleic acid using enzyme and the like (JP-A-6-271599); the method of binding a fluorescent substance-bound streptoavidin to a biotin-labelled nucleic acid; the method of reacting a fluorescent substance containing a group reactive with amine with an amino linker-bound nucleic acid; etc. However, these methods have such disadvantages that a fluorescent substance cannot be introduced into a naturally-occurring nucleic acid and complicated operation is required.

For example, JP-A-4-27867 describes a specific method of covalently binding a fluorescent rare earth metal chelate to a biological reactant, but this method is disadvantageous in that such a fluorescent rare earth metal chelate cannot be directly bound to a naturally-occurring nucleic acid via a covalent bond.

JP-A-6-94720 describes a method for photochemical labeling using a compound having a photoreactive group and a fluorescent rare earth metal chelate. However, this method is also disadvantageous in requiring a complicated step of ultraviolet irradiation.

Further, there is a method of intercalating a fluorescent substance to a double-stranded nucleic acid, which cannot be applied to labeling of a single-stranded nucleic acid.

SUMMARY OF THE INVENTION

An object of the present invention is to provide a novel fluorescent group-containing carbodiimide compound to be used as a label in a nucleic acid detection method or immunoassay, which can be easily handled, makes it possible to label efficiently for a short period of time, can be used to label a naturally-occurring nucleic acid, and has high sensitivity.

It is known that a carbodiimide compound reacts with a nucleic acid. For example, it is reported that a carbodiimide compound reacts with guanine and thymine which is not forming a hydrogen bond in a nucleic acid, to form an addition product [P. T. Gilham, J. Amer. Chem. Soc., 84, 688 (1962)].

As a result of intensive investigation of a method of simply and efficiently introducing a fluorescent group into a nucleic acid or a protein, the present inventors found that the above problems can be solved by introducing a fluorescent moiety to a carbodiimide compound utilizing high reactivity of a carbodiimide moiety with a nucleic acid, a protein and the like, to thereby achieve the present invention.

The present invention provides a fluorescent group-containing carbodiimide compound represented by the following formula (I):

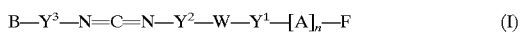

$$B-Y^3-N=C=N-Y^2-W-Y^1-[A]_n-F \quad (I)$$

wherein F represents a fluorescent group;

A represents a moiety selected from the group consisting of —CH$_2$—, —NHCO—, —CONH—, —O—, —S—, —NR—, wherein R is an alkyl group, —COO—, —OCO—, —NHSO$_2$—, and —SO$_2$NH—;

n is 0 or 1;

W represents a direct bond or a quaternary ammonium group;

Y$^1$, Y$^2$ and Y$^3$ each represents a group having the following formula (L):

$$-(CH_2)_p-L-(CH_2)_q- \quad (L)$$

wherein L is a direct bond or a moiety selected from the group consisting of —NHCO—, —CONH—, —O—, —S—, —NR—, —N$^+$RR'—, wherein R' is an alkyl group, —COO—, and —OCO—;

p and q each represents an integer of from 1 to 12; and

B represents a hydrogen atom or a monovalent organic group which may be the same as or different from that represented by —W—Y$^1$—[A]$_n$—F in the formula (I).

The present invention also provides the fluorescent group-containing carbodiimide compound represented by the following formula (II):

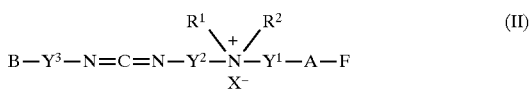

$$B-Y^3-N=C=N-Y^2-\overset{R^1\ \ R^2}{\underset{X^-}{N^+}}-Y^1-A-F \quad (II)$$

wherein R$^1$ and R$^2$ each represents a straight-chain or branched, saturated or unsaturated aliphatic hydrocarbon group having from 1 to 6 carbon atoms, a substituted or unsubstituted cycloalkyl group, a substituted or unsubstituted aryl group, a substituted or unsubstituted aralkyl group, or a nitrogen-containing heterocyclic group formed by R$^1$ and R$^2$ which are bound to each other;

X$^-$ represents a halogen atom or a sulfonate ion; and

B, Y$^1$, Y$^2$, Y$^3$, A and F have the same definition as in the above formula (I).

The present invention also provides the fluorescent group-containing carbodiimide compound represented by the above formula (II) which is a compound represented by the following formula (III):

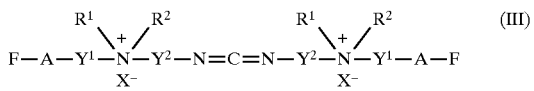

wherein $R^1$, $R^2$, $X^-$, $Y^1$, $Y^2$, A and F have the same definition as in the above formula (II).

The present invention also provides the fluorescent group-containing carbodiimide compound represented by the formula (IV):

wherein B and $Y^3$ have the same definition as in the above formula (I);

F' represents a moiety selected from the group consisting of a coumarin derivative, a pyrene derivative, a perylene derivative, a rhodamine derivative, a dansyl derivative, an oxazole derivative, and a thiazole orange derivative.

The present invention also provides the fluorescent group-containing carbodiimide compound represented by the formula (V):

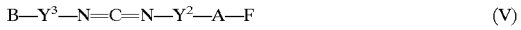

wherein B, $Y^2$, $Y^3$, A and F have the same definition as in the above formula (I).

The present invention also provides a process for producing the fluorescent group-containing carbodiimide compound represented by the formula (II) which comprises a step of reacting a carbodiimide group-containing compound represented by the formula (VI):

wherein W' represents a substituted or unsubstituted amino group; and B, $Y^3$, and $Y^2$ have the same definition as in the above formula (I), with a fluorescent group-containing compound represented by the formula (VII):

wherein F, A, and $Y^1$ have the same definition as in the above formula (I); and X is a halogen atom or a sulfonate group.

The present invention also provides a process for producing the fluorescent group-containing carbodiimide compound represented by the formula (IV) which comprises a step of reacting an amino group-containing fluorescent compound represented by the formula (VIII):

wherein F' has the same definition as in the above formula (IV), with an iso(thio)cyanate compound represented by the formula (IX):

wherein Z represents an oxygen atom or a sulfur atom; and B and $Y^3$ have the same definition as in the above formula (IV), to synthesize a (thio)urea compound represented by the formula (X):

wherein B, F, Z, and $Y^3$ have the same definition as in the above formulae (VIII) and (IX).

The present invention also provides a process for producing the fluorescent group-containing carbodiimide compound represented by the formula (V) which comprises a step of reacting an amino group-containing fluorescent compound represented by the formula (XI):

wherein F, A, and $Y^2$ have the same definition as in the above formula (V), with an iso(thio)cyanate compound represented by the formula (XII):

wherein Z represents an oxygen atom or a sulfur atom; and B and $Y^3$ have the same definition as in the above formula (V), to synthesize a (thio)urea compound represented by the formula (XIII):

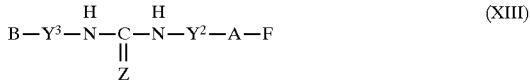

wherein A, B, F, Z, $Y^2$, and $Y^3$ have the same definition as in the above formulae (XI) and (XII).

Further, the present invention relates to a method for detecting a nucleic acid by hybridization using a labelled nucleic acid, wherein the above-described fluorescent group-containing carbodiimide compound is used as the label.

Furthermore, the present invention relates to a method for immunoassay using a labelled antigen or a labelled antibody, wherein the above-described fluorescent group-containing carbodiimide compound is used as the label.

Moreover, the present invention provides a method for peroxalate ester chemiluminescence assay utilizing chemiluminescence due to a reaction between an oxalic acid derivative and a peroxide in the presence of a fluorescent substance, wherein the fluorescent substance is the above-described fluorescent group-containing carbodiimide compound having the fluorescent moiety selected from the group consisting of a coumarin derivative, a pyrene derivative, a perylene derivative, a rhodamine derivative, a dansyl derivative, an oxazole derivative, a thiazole orange derivative, a cyanine compound, a benzothiazole derivative, a benzoxazole derivative, a benzoxadiazol derivative, a dipyrromethene borondifluoride derivative, and a fluorescent rare earth metal chelate compound.

The fluorescent group-containing carbodiimide compound represented by the formula (I) according to the present invention is a compound having a carbodiimide group which is highly reactive with a nucleic acid base, and a fluorescent moiety which has highly sensitive detection reactivity. It is useful as a label used in a nucleic acid detection method or a immunoassay, or a fluorescent substance used in a chemiluminescence assay.

DETAILED DESCRIPTION OF THE INVENTION

The embodiments of the present invention will be described in detail below.

(1) Fluorescent group-containing carbodiimide compound of the invention

The fluorescent group-containing carbodiimide compound of the present invention has the structure represented by the formula (I). Any of such a compound can be used as long as it has the structure in which a fluorescent moiety (F) is bound to a carbodiimide group optionally via a linker and the like.

The fluorescent moiety (F) in the formula (I) is not particularly limited as long as it is a fluorescent substance. Examples thereof include a moiety, selected from the group consisting of a coumarin derivative, a pyrene derivative, a perylene derivative, a rhodamine derivative, a dansyl derivative, an oxazole derivative, a cyanine compound, a benzothiazole derivative, a benzoxazole derivative, a benzoxadiazol derivative, and a dipyrromethene borondifluoride derivative. Such a fluorescent substance that its fluorescence intensity is increased by binding or intercalating to DNA or RNA, for example, a thiazole orange derivative, can also be used.

Further, a fluorescent rare earth metal chelate compound can be used. This compound is advantageous in that it enables the time-course degradation analysis because a metal ion which is stable for a long time is used as a fluorescent group and the compound has long fluorescence lifetime. Further, occurrence of background is infrequent and it can be easily detected even in a trace amount because an emission maxima is 500 nm or more as well as there is a large gap between the wavelength of the excitation light and the emitted light.

Specifically, the fluorescent moieties selected from the following groups represented by the formula (F) are preferably used:

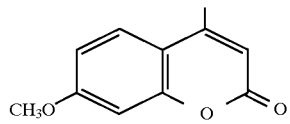
(F)

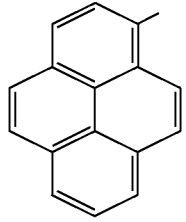

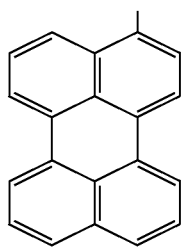

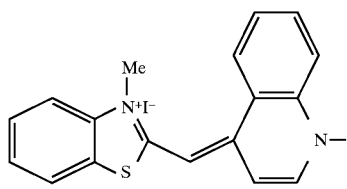

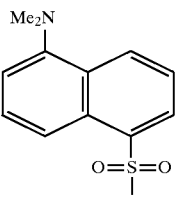

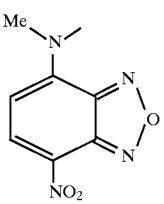

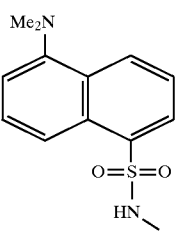

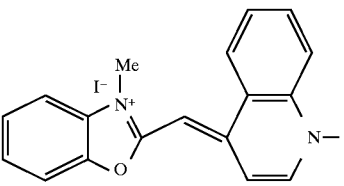

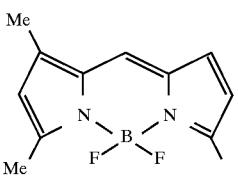

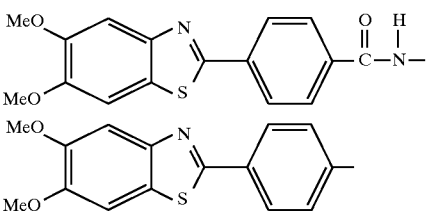

-continued

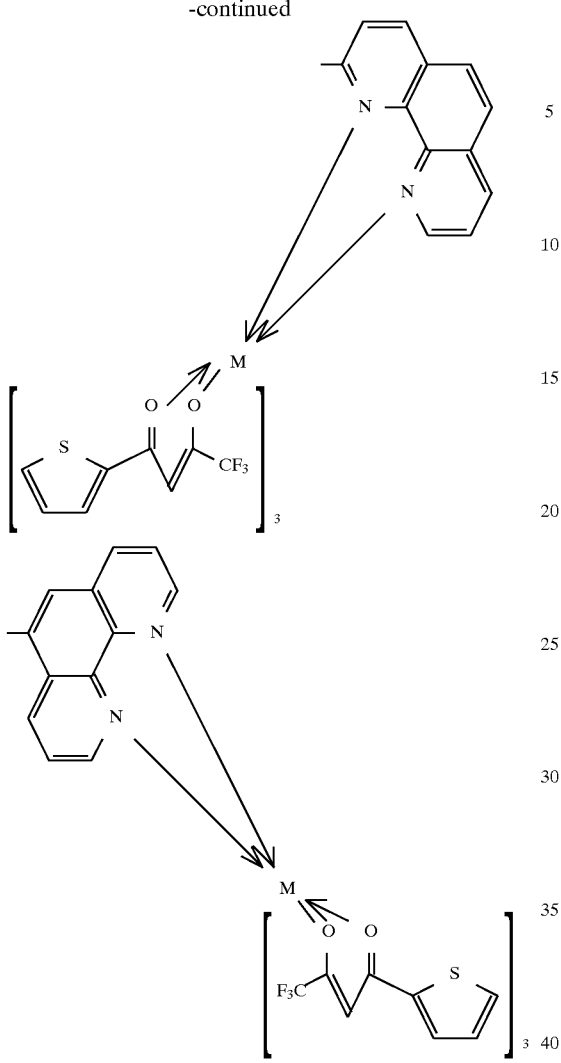

wherein M is $Eu^{3+}$, $Sm^+$, or $Tb^{3+}$.

Further, A in the formula (I) is a moiety selected from the group consisting of —$CH_2$—, —NHCO—, —CONH—, —O—, —S—, —NR—, wherein R is an alkyl group, —COO—, —OCO—, —$NHSO_2$—, and —$SO_2NH$—, preferably —$CH_2$—, —NHCO—, —CONH—, and the like. Examples of the alkyl group include a straight-chain or branched alkyl group having from 1 to 6 carbon atoms. n is 0 or 1. i.e., the moiety of A is optional in the compound represented by the formula (I).

W represents a direct bond or a quaternary ammonium group.

$Y^1$, $Y^2$ and $Y^3$ are a linker portion which binds a carbodiimide group to B, —A—F, or the like, and each represents a group shown by the formula (L). In the formula (L), L is a direct bond or a moiety selected from the group consisting of —NHCO—, —CONH—, —O—, —S—, —NR—, —$N^+RR'$—, wherein R' is an alkyl group, —COO—, and —OCO—. Examples of the alkyl group include a straight-chain or branched alkyl group having from 1 to 6 carbon atoms. p and q each represents 0 or an integer of from 1 to 12. Preferable examples of $Y^1$, $Y^2$ and $Y^3$ include a direct bond or an alkylene group have 1 to 12 carbon atoms which may optionally have a methyl group as a side chain or in the main chain. Examples of the alkylene group include methylene, ethylene, trimethylene, 1-methyltrimethylene, tetramethylene, 1-methyltetramethylene, 2,2-dimethyltrimethylene, pentamethylene, and the like. These alkylene groups may be bound to each other through a moiety selected from the group consisting of —NHCO—, —CONH—, —O—, —S—, —NR—, —$N^+RR'$—, —COO—, and —OCO—.

B represents a hydrogen atom or a monovalent organic group. The monovalent organic group may be the same as or different from —W—$Y^1$—A—F in the formula (I). Preferably, it represents an alkyl group, a tertiary amino group, or a quaternary ammonium group. More preferable examples thereof are listed below.

(A) A nitrogen-containing heterocyclic group in which a nitrogen atom may be quaternarized with a hydrogen atom, a saturated or unsaturated hydrocarbon group, an aryl group, an aralkyl group, or an organic group having a fluorescent group F, such as a pyridyl group, a pyridinium group, a pyrrolidyl group, a pyrrolidinium group, a piperidilyl group or a piperidinium group, particularly, 2-, 3-, or 4-pyridyl group, or pyridinium group, 2- or 3-pyrrolidyl group or pyrrolidinium group, or 2-, 3-, or 4-piperidilyl group or piperidinium group, in which a nitrogen atom may be quaternarized with a $C_1$–$C_{10}$ alkyl group, such as a methyl group;

(B) An amino group in which a nitrogen atom may be quaternarized with a hydrogen atom, a saturated or unsaturated hydrocarbon group, an aryl group, an aralkyl group, or an organic group having a fluorescent group F, particularly, an amino group in which a nitrogen atom may be quaternarized with a group containing a $C_1$–$C_{10}$ alkyl group, specifically a dimethylamino group, a diethylamino group, and a diisopropylamino group.

(C) A heterocyclic tertiary amino group, a heterocyclic tertiary or quaternary ammonium group, represented by the following formula:

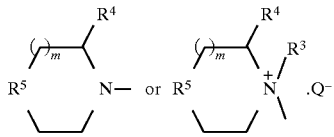

wherein $R^3$ and $R^4$ each represents a hydrogen atom, a $C_1$–$C_{10}$ straight-chain or branched aliphatic hydrocarbon group, a substituted or unsubstituted aryl group, or a substituted or unsubstituted aralkyl group, particularly, a $C_1$–$C_{10}$ alkyl group, a phenyl group, or a phenyl group substituted with a $C_1$–$C_{10}$ alkyl group. Q represents an anion, such as a sulfate ion, an alkylsulfate ion, an arylsulfate ion, a halosulfate ion, a halide ion, and the like. $R^5$ represents an oxygen atom, a sulfur atom, or a methylene group. m is 0 or 1. Specifically, a group represented by the following formula:

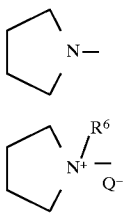

-continued

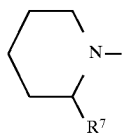

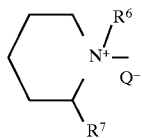

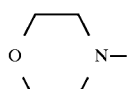

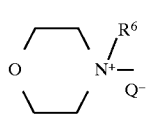

wherein $R^6$ and $R^7$ each represents a hydrogen atom, a $C_1$–$C_{10}$ alkyl group, a phenyl group, or a phenyl group substituted with a $C_1$–$C_{10}$ alkyl group.

(D) A substituted or unsubstituted alkyl group, such as a methyl group, an ethyl group, a propyl group, an isopropyl group, a butyl group, a sec-butyl group, a tert-butyl group, or a cyclohexyl group, a phenyl group, and the like.

Preferable examples of these carbodiimide compounds represented by the formula (I) include the compounds listed in (a), (b), and (c) below.

(a) Compounds represented by the formula (II)

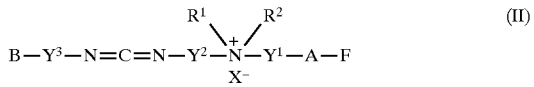

These compounds are those represented by the formula (I) in which W is a quaternary ammonium group. In the formula (II), $R^1$ and $R^2$ each represents a straight-chain or branched, saturated or unsaturated aliphatic hydrocarbon group C1–C6, a substituted or unsubstituted cycloalkyl group, a substituted or unsubstituted aryl group, or a substituted or unsubstituted aralkyl group. $R^1$ and $R^2$ may be the same or different. Examples of the aliphatic hydrocarbon group include an alkyl group, an alkenyl group, an alkynyl group, and a cycloalkyl group. The alkyl group includes a methyl group, an ethyl group, a propyl group, an isopropyl group, a butyl group, an isobutyl group, a sec-butyl group, a tert-butyl group, a pentyl group, an isopentyl group, a hexyl group, and the like. Among these, a methyl group is preferred.

The alkenyl group includes vinyl group, allyl group, crotyl group, tiglyl group, prenyl group, and the like. Particularly, those having from 2 to 5 carbon atoms are preferred. The alkynyl group includes an ethynyl group, a propargyl group, and the like, and those having from 2 to 5 carbon atoms are particularly preferred. The cycloalkyl group may optionally have on its ring a substituent such as an alkyl group. Examples thereof include cyclopropyl, cyclopentyl, cyclohexyl, 4-methylcyclohexyl, 4-tert-butylcyclohexyl, cyclooctyl, and the like. Those having from 6 to 10 carbon atoms are particularly preferred.

The aryl group may be either monocyclic or polycyclic, and includes, for example, phenyl, naphthyl, and the like. The aralkyl group includes benzyl, phenethyl, and the like. $R^1$ and $R^2$ may be bound to each other to form a nitrogen-containing heterocyclic group. Examples of such a nitrogen-containing heterocyclic group include a pyridinium group, a pyrrolidium group, a piperidium group, a piperazinium group, a morpholino group, and the like.

In the formula (II), $X^-$ represents a halogen ion or a sulfonate ion. The sulfonate ion may be substituted with an alkyl group, an aryl group, and the like. Examples of $X^-$ include $Br^-$, $Cl^-$, $I^-$, $MeSO_3^-$, $TsO^-$ (p-toluenesulfonate ion), and the like.

Specific examples of B, $Y^1$, $Y^2$, $Y^3$, F, and A are the same as those in the above formula (I). B may be the same organic group as the monovalent organic group represented by —W—$Y^1$—A—F in the formula (I) (where W, $Y^1$, A and F have the same definition as in the formula (I)). When it is the same, it can be a carbodiimide compound having a structure symmetrical about the carbodiimide group, which is, for example, represented by the formula (III).

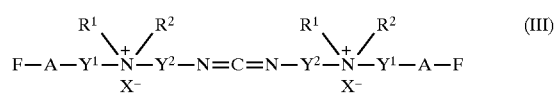

Specific examples of the compounds represented by the formulae (II) and (III) are shown below.

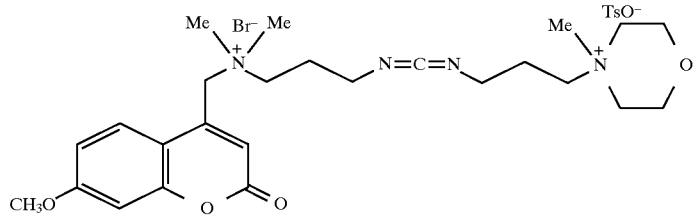

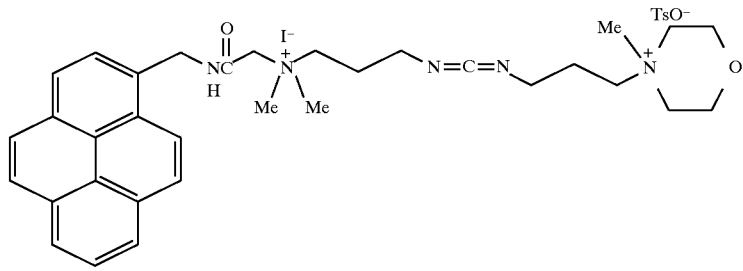

-continued
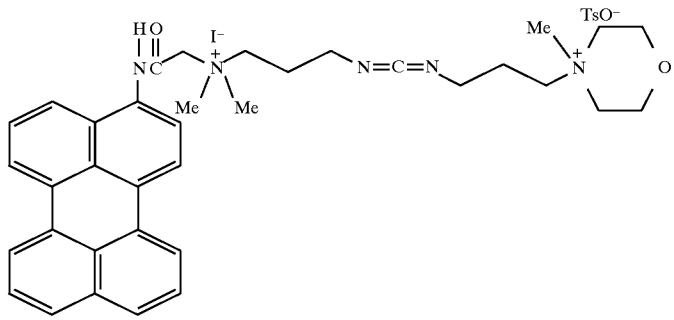
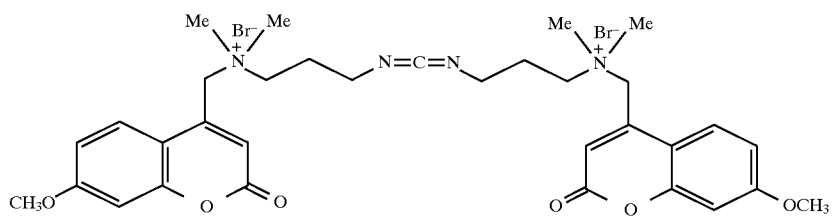
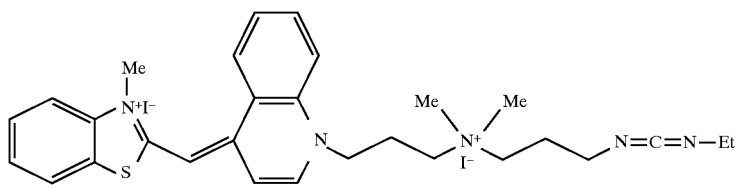
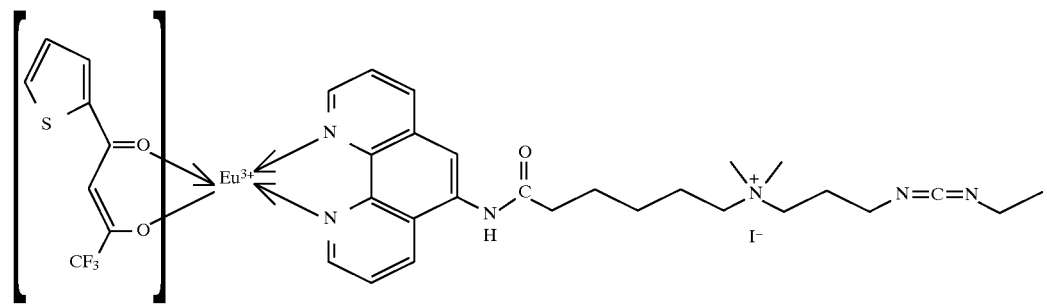
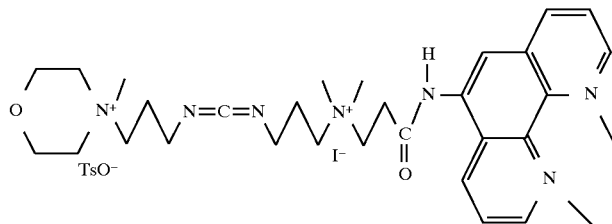
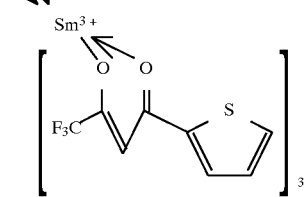

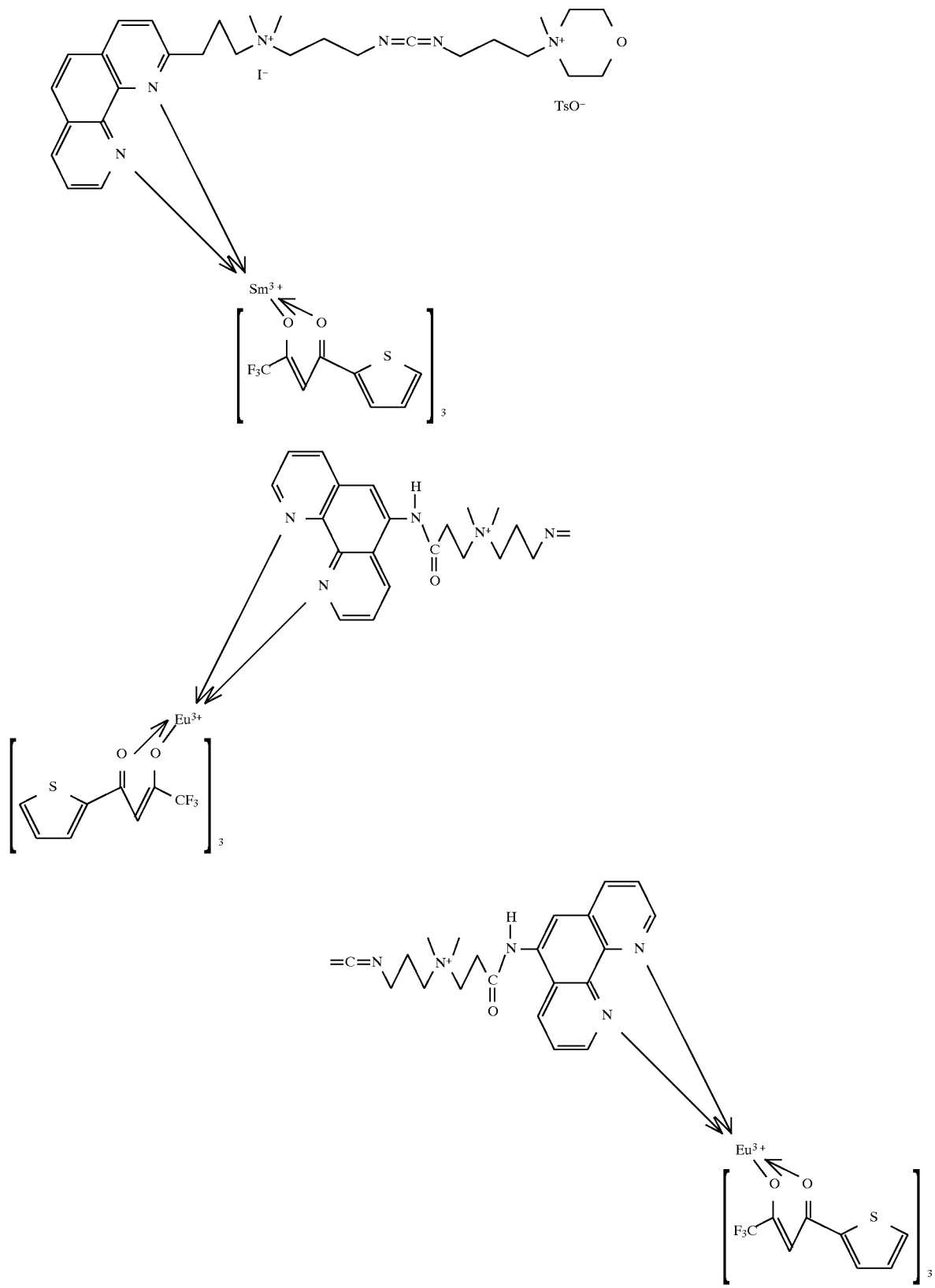

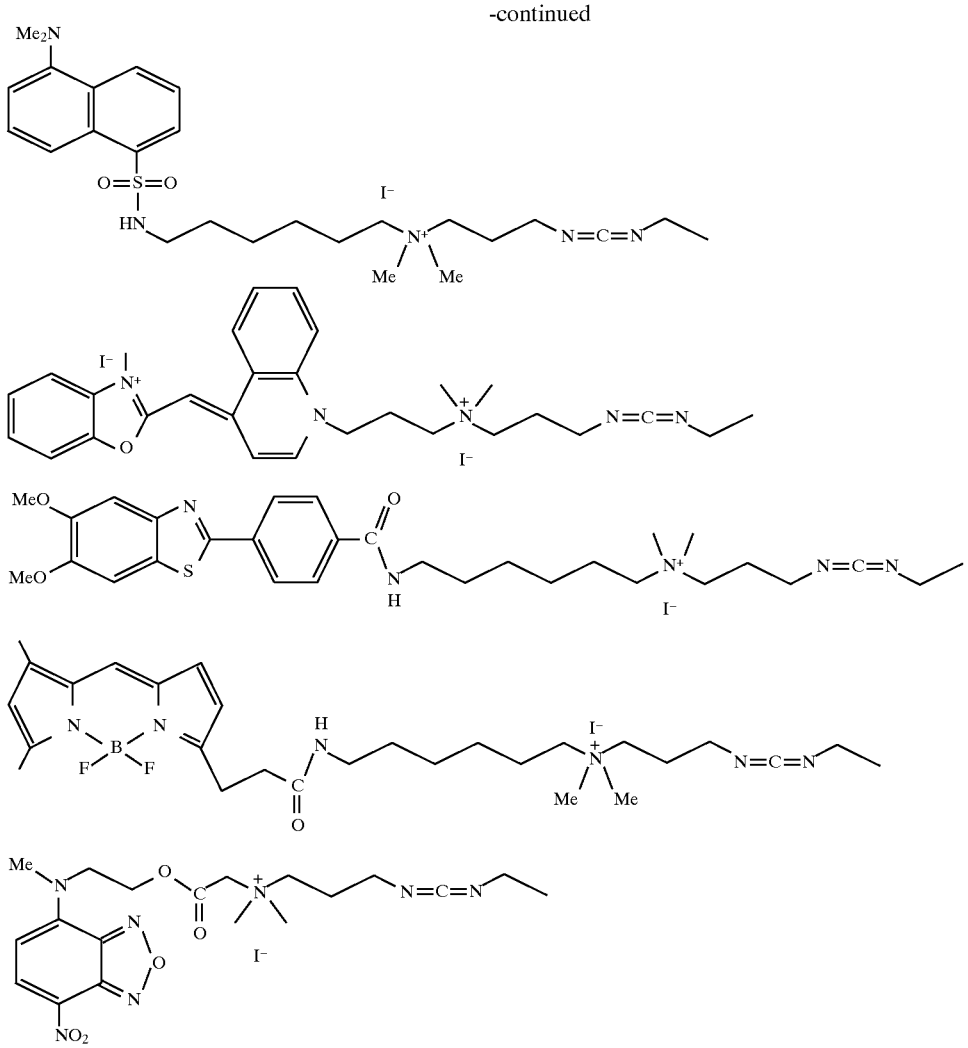

wherein Me represents a methyl group, and TsO⁻ represents a toluenesulfonate ion.

(b) Compounds represented by the formula (IV)

(IV)

In the formula (IV), B and $Y^3$ have the same definition as those in the above formula (I). The fluorescent group F' can be selected from those described in (a) above. Preferably, it can be selected from the group consisting of a coumarin derivative, a pyrene derivative, a perylene derivative, a rhodamine derivative, a dansyl derivative, an oxazole derivative, a thiazole orange derivative, and the like. Specifically, the fluorescent groups represented by the following formula (F'') can be preferably used.

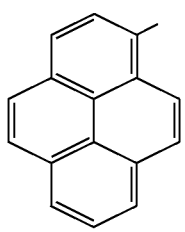
(F'')

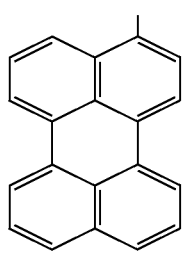

Specific examples of the compounds represented by the formula (IV) are shown below.

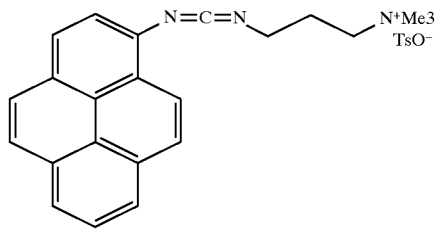

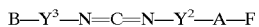

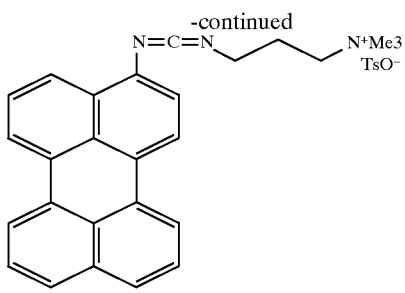

wherein Me represents a methyl group, and TsO⁻ represents a p-toluenesulfonate ion.

(c) Compounds represented by the formula (V)

In the formula (V), specific examples of A, B, $Y^2$, and $Y^3$ are the same as those in the above formula (I). A preferably represents —NHCO— or —CONH—. The fluorescent group F can be selected from those described in (a) above, preferably, a coumarin derivative, a pyrene derivative, a perylene derivative, a rhodamine derivative, a dansyl derivative, an oxazole derivative, a cyanine compound, a benzothiazole derivative, a benzoxazole derivative, a benzoxadiazol derivative, a dipyrromethene borondifluoride derivative, a fluorescent rare earth metal chelate compound, and the like. Specific examples of these compounds represented by the formula (V) are shown below.

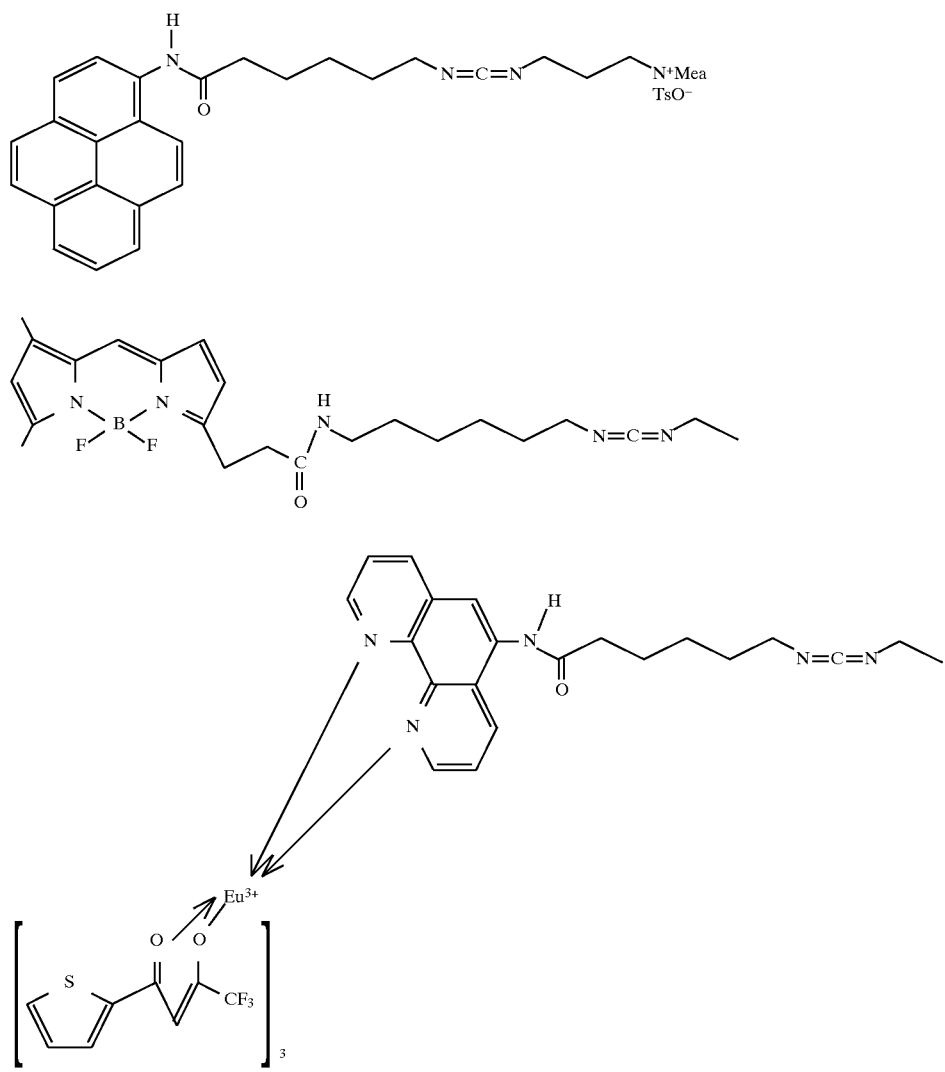

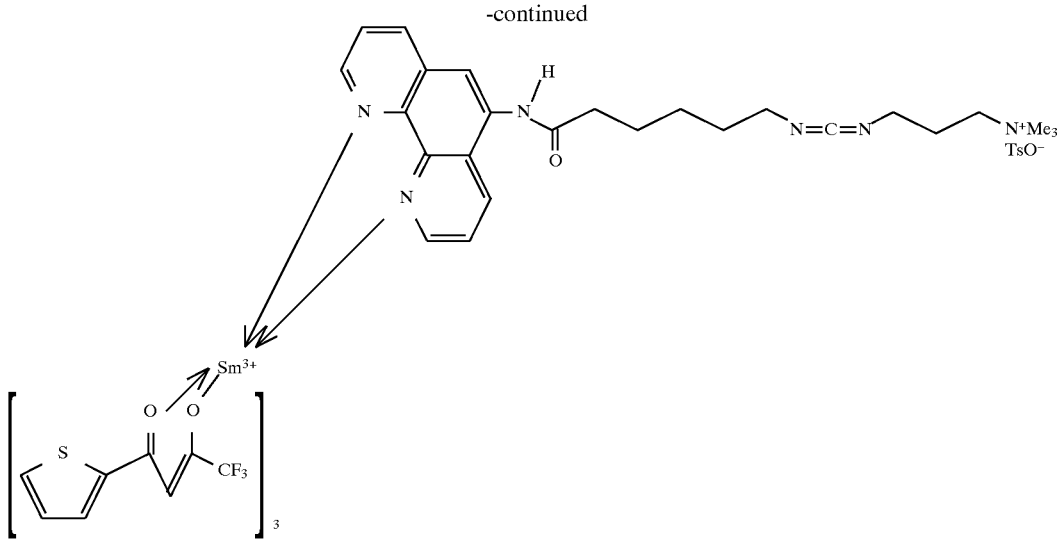

wherein Me represents a methyl group, and TsO⁻ represents a p-toluenesulfonate ion.

(2) Process for producing the fluorescent group-containing carbodiimide compound of the invention The process for producing the carbodiimide compound of the present invention represented by the formula (I) includes the following methods.

(i) Process for producing compounds represented by the formula (II)

First of all, a process for producing the fluorescent group-containing carbodiimide compound represented by the formula (I) which is the compound represented by the formula (II).

The fluorescent group-containing carbodiimide compound represented by the formula (II) can be produced by the method comprising a step of reacting the carbodiimide group-containing compound represented by the formula (VI) with the fluorescent group-containing compound represented by the formula (VII). Namely, the carbodiimide group-containing compound represented by the formula (VI) has an amino group (W') at its end, which reacts with a halogen atom or a sulfonate group (X) at the end of the fluorescent group-containing compound represented by the formula (VII) to bind to each other.

B, Y², and Y³ in the formula (VI), and F in the formula (VII) have the same definition as those in the above formula (I). The carbodiimide group-containing compound represented by the formula (VI), and the fluorescent group-containing compound represented by the formula (VII) can be selected depending on the desired structure of the fluorescent group-containing carbodiimide compound. For example, the carbodiimide group-containing compound represented by the formula (VI) includes N-3-dimethylaminopropyl-N'-3-(4-morpholino)-propylcarbodiimide, 1-ethyl-3,3-dimethylaminopropylcarbodiimide, bis-(3,3-dimethylaminopropyl)carbodiimide, and the like. Such carbodiimide group-containing compounds can be usually obtained by leading an amine compound which is used as a starting material, such as a primary amine derivative, to a urea or thiourea derivative, and converting it to include a carbodiimide moiety through dehydration or oxidative desulfurization. A symmetrical carbodiimide compound can be synthesized utilizing condensation reaction accompanied with decarbonation from an isocyanate compound.

For example, as shown in the reaction formula below, an amine compound (a) is condensed with urea to give a 1-substituted urea (b), which is reacted with the second primary amine (c) which may be same as or different from the amino compound (a), to synthesize a 2-substituted urea intermediate (d). Namely, the amine compound (a) or a salt thereof is reacted with urea for several hours under heating in water or an appropriate solvent, then the 1-substituted urea (b) is isolated or add the other or the same amine compound in the reaction mixture, and the reaction is allowed to proceed under the same conditions to synthesize the 2-substituted urea intermediate [T. L. Davis and K. C. Blanchard, Org. Synth. Coll., Vol. 1, 453 (1941)].

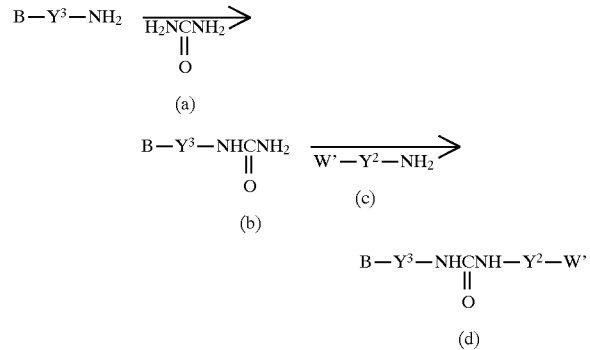

The 1-substituted urea (b) is reacted with the second amino compound (c) under the same conditions, wherein the 1-substituted urea (b) may be isolated prior to the reaction or the second amino compound (c) may be added in the reaction mixture containing 1-substituted urea (b). Alternatively, the 1-substituted urea (b) can be synthesized by reacting the amine compound (a) with a cyanic acid or its salt [F. Kurzer, Org. Synth. Coll., Vol. 4, 49 (1963)].

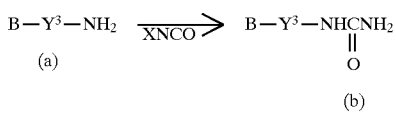

The thus-obtained 1-substituted urea derivative (b) can be converted into the 2-substituted derivative (d) by the above-described method. The 2-substituted urea derivative (d) can be directly obtained by utilizing reaction between an amine compound (a) or (c) and an isocyanate compound (e) [J. H. Saunders and R. Slocombe, Chem. Rev., 43, 203 (1948)].

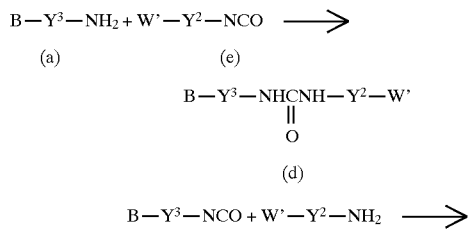

On the other hand, a thiourea derivative (g) is generally synthesized by reacting an amine compound with an isothiocyanate compound (f) [N. A. Ivanov, R. V. Viasova, V. A. Gancharava, and L. N. Smirov, Izv. Vyssh. Uchebn. Zaved. Khim. Khim. Tekhnol., 19(7), 1010 (1976)].

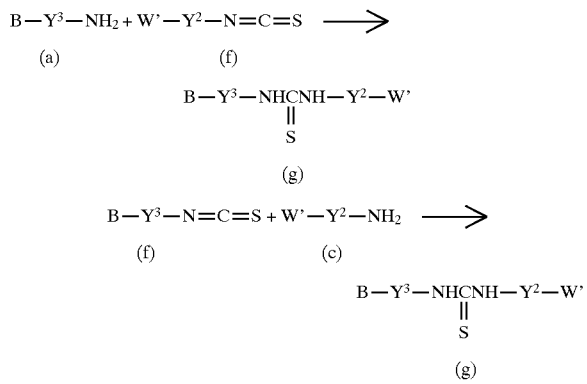

Further, a symmetrical thiourea compound can be synthesized by reaction between an amine compound (a) and carbon disulfide [W. W. Levis, Jr. and E. A. Waipert, U.S. Pat. No. 3,168,560 (1965)].

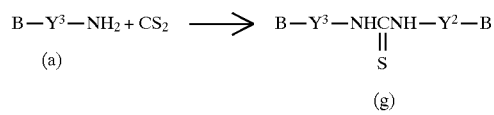

The thus-obtained 2-substituted urea derivative (d) and thiourea derivative (g) can be led to a carbodiimide group-containing compound (VI) by dehydration or oxidative desulfurization.

Synthesis of the carbodiimide group-containing compound from the urea derivative (d) by dehydration can be easily effected by heating the urea derivative with p-toluenesulfonic chloride (TSCl) in the presence of tertiary amine [G. Amiard and R. Heymes, Bull. Soc. Chim. Fr., 1360 (1956)].

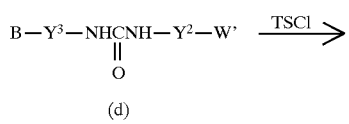

-continued
$$B—Y^3—N=C=N—Y^2—W'$$
(VI)

Dehydration of the 2-substituted urea derivative (d) can be carried out using p-toluenesulfonic chloride and potassium carbonate in the presence of a quaternary ammonium salt [Zsuzsa M. Jaszay et al., Synthesis, 520 (1987)].

Generally, the thiourea derivative (g) can be desulfurized using mercury oxide as a desulfurizing agent. Solvents preferably used in this reaction include ether, benzene, acetone, and the like.

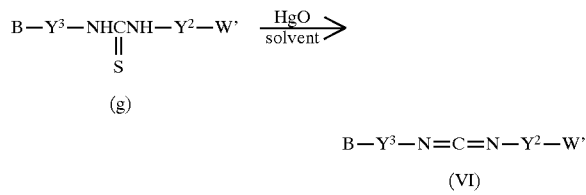

$$B—Y^3—N=C=N—Y^2—W'$$
(VI)

In addition to mercury oxide, examples of the desulfurizing agent include lead oxide [F. Zetzehe and A. Fredrich, Chem. Ber., 73, 1114 (1940)], zinc oxide [R. F. Coles, U.S. Pat. No. 2,946,819 (1960)], lead carbonate, lead nitrate, lead chloride [J. C. Sheehan, U.S. Pat. No. 3,135,748 (1964)], and the like. It can be synthesized by using sodium hypochlorite under alkaline conditions [H. Stetter and C. Wulff, Chem. Ber., 95, 2302 (1962)]. For example, the thiourea derivative is allowed to react with sodium hypochlorite, sodium carbonate, and copper chloride in a solvent such as methylene chloride at 0° C. or less over a day and a night, followed by carrying out isolation and purification by the conventional methods to obtain the carbodiimide group-containing compound (VI).

The thus-obtained carbodiimide group-containing compound (VI) is reacted with the fluorescent group-containing compound (VII) as described below to produce the fluorescent group-containing carbodiimide compound represented by the formula (I). In the formula (VII), X represents a halogen atom, or a substituted or unsubstituted sulfonate group, preferably bromine or iodine.

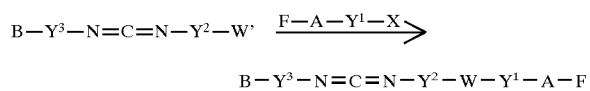

These reaction steps can be carried out by the known methods using a solvent commonly used such as dimethylformamide (DMF), acetone, benzene, dimethylsulfoxide (DMSO), dichloromethane, and the like. The above-described reaction between the carbodiimide group-containing compound (VI) and the fluorescent group-containing compound (VII) can be carried out using a solvent commonly used such as dimethylformamide, dichloromethane, DMSO, and the like.

Further, the resulting fluorescent group-containing carbodiimide compound is reacted with methyl p-toluenesufonate (TsOMe), methyl iodide, dimethylsulfate, or the like in a solvent such as dimethylformamide to introduce a quaternary ammonium group into the portion of B, thereby obtaining the fluorescent group-containing carbodiimide compound which have improved water-solubility.

The amine compound to be used is a compound having a substituted or unsubstituted amino group, such as 4-(3-aminopropyl)morpholine, N,N-dimethylpropanediamine, and the like.

The isocyanate compound includes cyclohexylisocyanate, n-butylisocyanate, and the like.

The isothiocyanate compound includes dialkylamino group containing isothiocyanate compounds, alkylaminoisothiocyanate compounds, and the like. Specific examples thereof are 3-dimethylaminopropylisothiocyanate, 3-diethylaminopropylisothiocyanate, and the like.

Examples of the fluorescent group-containing compound (VII) include 4-bromomethyl-7-methoxycoumarin, N-((2-(iodoacetyl)-ethyl)-N-methyl)amino-7-nitrobenz-oxa -1,3-diazole, 5-iodoacetamidotetramethylrhodamine, and the like.

(ii) Process for producing compounds represented by the formula (IV)

The process for producing the fluorescent group-containing carbodiimide compound represented by the formula (I) which is a compound represented by the formula (IV) is illustrated below.

The fluorescent group-containing carbodiimide compound represented by the formula (IV) can be produced by the method comprising a step of reacting the amino group-containing fluorescent compound represented by the formula (VIII) with the iso(thio)cyanate compound represented by the formula (IX) to synthesize a (thio)urea compound represented by the formula (X). In other words, an amine derivative is reacted with an iso(thio)cyanate compound to lead it to a urea or a thiourea derivative, followed by dehydration or oxidative desulfurization to form a carbodiimide group.

This reaction is shown in the following reaction formula:

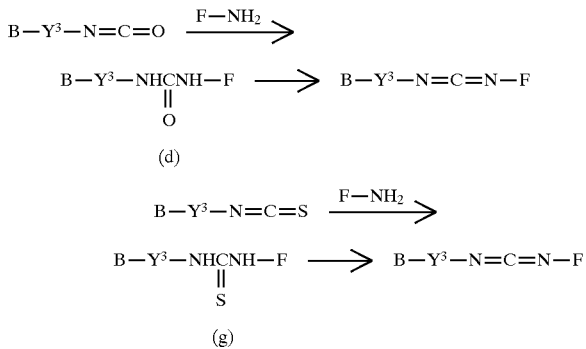

The synthesis of the carbodiimide group-containing compound from the urea derivative (d) by dehydration can be easily effected by heating the urea derivative with p-toluenesulfonic chloride (TSCl) in the presence of a tertiary amine in the same manner as described in the synthesis of the compound represented by the formula (II). It can also be carried out using p-toluenesulfonic chloride and potassium carbonate in the presence of a quaternary ammonium salt.

Generally, the thiourea derivative (g) can be desulfurized using mercury oxide as a desulfurizing agent in the same manner as described in the synthesis of the compound represented by the formula (II). Solvents preferably used in this reaction include ether, benzene, acetone, and the like. Examples of the desulfurizing agent in addition to mercury oxide include lead oxide, zinc oxide, lead carbonate, lead nitrate, lead chloride, and the like. It can be synthesized by using sodium hypochlorite under alkaline conditions. For example, the thiourea derivative is allowed to react with sodium hypochlorite, sodium carbonate, and copper chloride in a solvent such as methylene chloride at 0° C. or less over a day and a night, followed by carrying out isolation and purification by the conventional methods to obtain the carbodiimide compound (IV). These reaction steps can be carried out by the known methods using a solvent commonly used such as dimethylformamide (DMF), acetone, benzene, dichloromethane, and the like.

Further, the resulting fluorescent group-containing carbodiimide compound is reacted with methyl p-toluenesufonate (TsOMe), methyl iodide, dimethylsulfate, or the like in a solvent such as dimethylformamide to introduce a desired quaternary ammonium group.

The amino group-containing fluorescent compound (VIII) and the iso(thio)cyanate compound (IX) can be selected depending on a desired structure of the fluorescent group-containing carbodiimide compound. Examples of the amino group-containing fluorescent compound (VIII) include 1-aminopyrene, 1-aminoperylene, and the like. Examples of the iso(thio)cyanate compound (IX) include 3,3-dimethylaminopropylisocyanate, 3,3-diethylaminopropylisocyanate, 3-morpholinopropylisocyanate, 3,3-dimethylaminopropylisothiocyanate, 3,3-diethylaminopropylisothiocyanate, 3-morpholinopropylisothiocyanate, and the like.

Examples of the (thio)urea compound (X) obtained by reacting the amino group-containing fluorescent compound (VIII) with the iso(thio)cyanate compound (IX) includes N-pyrenyl-N'-(3-dimethylamino)propylurea, N-perylenyl-N'-(3,3-dimethylamino)propylurea, N-pyrenyl-N'-(3-dimethylamino)propylthiourea, N-perylenyl-N'(3,3-dimethylamino)propylthiourea, and the like.

(iii) Process for producing compounds represented by the formula (V)

The process for producing the fluorescent group-containing carbodiimide compound represented by the formula (I) which is a compound represented by the formula (V) is illustrated below.

The fluorescent group-containing carbodiimide compound represented by the formula (V) can be produced by the method comprising a step of reacting the amino group-containing fluorescent compound represented by the above formula (XI) with the iso(thio)cyanate compound represented by the above formula (XII) to synthesize a (thio)urea compound represented by the following formula (XIII). In other words, an amine derivative is reacted with an iso(thio) cyanate compound to lead it to a urea or a thiourea derivative, followed by dehydration or oxidative desulfurization to form a carbodiimide group, in the same manner as described in (ii) above. This reaction is shown by the following reaction formula:

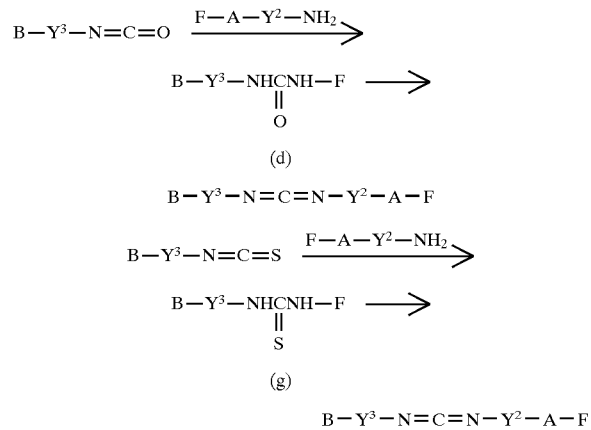

The synthesis of the carbodiimide group-containing compound from the urea derivative (d) by dehydration can be easily effected by heating the urea derivative with p-toluenesulfonic chloride (TSCl) in the presence of a tertiary amine, in the same manner as in (ii) above. It can also be carried out using p-toluenesulfonic chloride and potassium carbonate in the presence of a quaternary ammonium salt.

Generally, the thiourea derivative (g) can be desulfurized using mercury oxide as a desulfurizing agent. Solvents preferably used in this reaction include ether, benzene, acetone, and the like. Examples of the desulfurizing agent in addition to mercury oxide include lead oxide, zinc oxide, lead carbonate, lead nitrate, lead chloride, and the like. It can be synthesized by using sodium chloride under alkaline conditions. For example, the thiourea derivative is allowed to react with sodium hypochlorite, sodium carbonate, and copper chloride in a solvent such as methylene chloride at 0° C. or less over a day and a night, followed by carrying out isolation and purification by the conventional methods to obtain the carbodiimide compound (V). These reaction steps can be carried out by the known methods using a solvent commonly used such as dimethylformamide (DMF), acetone, benzene, dichloromethane, and the like.

Further, the resulting fluorescent group-containing carbodiimide compound may be reacted with methyl p-toluenesufonate (TsOMe), methyl iodide, dimethylsulfate, or the like in a solvent such as dimethylformamide to introduce a desired quaternary ammonium group.

The amino group-containing fluorescent compound (XI) and the iso(thio)cyanate compound (XII) can be selected depending on a desired structure of the fluorescent group-containing carbodiimide compound. Examples of the amino group-containing fluorescent compound (XI) include N-pyrenyl-6-aminocaprylamide, N-perylenyl-6-aminocaprylamide, and the like. These amino group-containing fluorescent group can be obtained by reacting a fluorescent compound such as 1-aminopyrene, 1-aminoperylene, and the like with a carboxyl group-containing compound such as 6-aminocaproic acid in the conventional manner.

Examples of the iso(thio)cyanate compound (XII) include 3,3-dimethylaminopropylisocyanate, 3,3-diethylaminopropylisocyanate, 3-morpholinopropylisocyanate, 3,3-dimethylaminopropylisothiocyanate, 3,3-diethylaminopropylisothiocyanate, 3-morpholinopropylisothiocyanate, and the like.

The fluorescent group-containing carbodiimide compound of the present invention obtained by the above methods can be suitably used as the label in a nucleic acid detection method and immunoassay. In this case, the fluorescent group-containing carbodiimide compound of the present invention can be brought into contact with a nucleic acid such as DNA or a protein such as antigen or antibody to be labelled by mixing these compounds in a solvent to bind to each other. Namely, a fluorescent substance, which is a highly sensitive detection reagent, can be attached as the label to a substance to be labelled including a nucleic acid or a protein by binding the carbodiimide group, which is highly reactive with a nucleic acid base, of the fluorescent group-containing carbodiimide compound of the present invention to the nucleic acid or the protein. In the case of binding the fluorescent group-containing carbodiimide compound of the present invention to a nucleic acid or a protein, the carbodiimide group is preferably contacted under its reactive condition, for example, under alkaline conditions such as about pH 7.5 to 8.5.

(3) Nucleic acid detection method of the invention

The fluorescent group-containing carbodiimide compound of the present invention can be used as the label in the nucleic acid detection method by hybridization using a labelled nucleic acid. Namely, the nucleic acid labelled with the fluorescent group-containing carbodiimide compound can be used as a probe for hybridization. The nucleic acid to be assayed can be detected by allowing the nucleic acid to hybridize with the probe to form a nucleic acid-nucleic acid hybrid, removing free probe from the system, and detecting the label contained in the hybrid. In the present invention, the fluorescent group-containing carbodiimide compound used as the label can be directly detected by measuring fluorescence intensity using a fluorospectrophotometer, a fluorospectrophotometer for 96-well microtiter plate, a fluorescence microscope, and the like. The nucleic acid to be assayed is usually immobilized on a membrane such as nylon membrane and nitrocellulose, or a microtiter plate, prior to measure.

For hybridization in the nucleic acid detection method according to the present invention, any common nucleic acid hybridization method can be used, including colony hybridization, plaque hybridization, dot blot hybridization, Southern hybridization, Northern hybridization, and the like, except for using the fluorescent group-containing carbodiimide compound as the label for a nucleic acid probe. The nucleic acid to be assayed may be either DNA or RNA. The nucleic acid used as a probe may also be either DNA or RNA.

Labeling of a nucleic acid used as a probe can be preferably carried out by binding the label to polynucleotide or oligonucleotide using the above method. Alternatively, labelled nucleotide can be incorporated into polynucleotide or oligonucleotide by the polymerase reaction.

(4) Immunoassay of the invention

The above-described fluorescent group-containing carbodiimide compound of the present invention can be used as the label in immunoassay using a labelled antigen or a labelled antibody.

When an antigen is to be assayed, it can be detected by labeling an antibody which is specifically bound to the antigen, forming an antigen-antibody complex, then removing free antibody from the system, and detecting the label contained in the complex. In the present invention, the fluorescent group-containing carbodiimide compound to be used as the label can be directly detected by measuring fluorescence intensity using a fluorospectrophotometer, a fluorospectrophotometer for microtiter plate, a fluorescence microscope, and the like. Alternatively, a first antibody which is specifically bound to the antigen is immobilized and allowed to bind to the antigen, then a labelled second antibody which is specifically bound to the antigen is further allowed to bind thereto. In this case, the first antibody and the second antibody may be the same polyclonal antibody, or different monoclonal antibodies. Further, one of them may be polyclonal antibody, and the other may be monoclonal antibody. In each case, alternatively, an unlabelled antibody may be used in place of a labelled antibody, an antigen is allowed to bind thereto, and a labelled second antibody which is specifically bound to the antibody is further allowed to bind thereto. Immunoglobulin derived from an animal which is used in preparing an antibody can be used to immunize a different animal to obtain the second antibody.

When an antibody is to be assayed, it can be detected by labeling an antigen which is specifically bound to the antibody, forming an antigen-antibody complex, then removing free antigen from the system, and detecting the label contained in the complex. When an antibody which is specifically bound to the antibody to be assayed can be obtained, it may be labelled and used to form an antibody-antibody complex.

Any commonly used procedure of immunoassay can be applied to the immunoassay of the present invention, except for using the fluorescent group-containing carbodiimide compound as the label for an antigen or an antibody. Immobilization of an antigen or an antibody, antigen-antibody reaction, washing procedure, and the like can be carried out in the same manner as in the commonly used methods. Any method of immunoassay including the direct method, the indirect method, the competitive method, and the like can be applied.

(5) Chemiluminescence assay of the invention

The chemiluminescence assay of the present invention utilizes chemiluminescence emitted when a oxalic acid derivative is reacted with peroxide in the presence of a fluorescent substance. Specifically, peroxide or a fluorescent substance can be determined by measuring fluorescence intensity generated in the emission reaction among the oxalic acid derivative, peroxide, and the fluorescent substance. The fluorescent group-containing carbodiimide compound of the present invention can be used as the fluorescent substance, particularly those having a fluorescent moiety selected from the group consisting of a coumarin derivative, a pyrene derivative, a perylene derivative, a rhodamine derivative, a dansyl derivative, an oxazole derivative, a thiazole orange derivative, a cyanine compound, a benzothiazole derivative, a benzoxazole derivative, a benzoxadiazol derivative, a dipyrromethene borondifluoride derivative, and a fluorescent rare earth metal chelate compound, and the like.

The mechanism for generating chemiluminescence is presumed that a peroxalic acid derivative produced by reaction between an oxalic acid derivative and peroxide is converted into a substituted 1,2-dioxetane by rearrangement, which forms a complex together with a fluorescent substance, which is easily oxidized, due to transfer of electric charge, the excitation of the fluorescent substance was caused by transfer of electrons, and it emits light as a result of the return to the ground state. The oxalic acid derivative to be used includes oxalic acid esters such as aryl oxalate, and the like. As the peroxide, hydrogen peroxide is preferably used. Such chemiluminescence, which is called peroxalate chemiluminescence, is superior in emission efficiency to the conventional chemiluminescence, and therefore, it is widely applied to analytical chemistry.

The chemiluminescence assay of the present invention provides high emission efficiency and does not require the light source for exciting the fluorescent substance, which results in few noise. Thus, the chemiluminescnece assay of the present invention enables detection of very low level of emission and provides excellent sensitivity. Since the amount of emission increases in proportion to the concentrations of the fluorescent substance and peroxide, these substances can be determined utilizing such property. For example, a trace amount of peroxide can be determined by selecting an appropriate fluorescent substance. In the case of using an enzymatic reaction in which hydrogen peroxide is formed, a substrate can be determined by measuring hydrogen peroxide thus formed. Using such reaction systems, quantification can be made for glucose, lactose, NADH, uric acid, formaldehyde, cholesterol, α-amino acid, acetylcholine, and the like.

Further, the substance to be assayed can be detected with high sensitivity using the chemiluminescence assay of the present invention by introducing a fluorescent group to the substance to be assayed such as an amino acid and the like. For example, when an oxalic acid derivative and peroxide are used in a large excess amount, one fluorescent molecule can emit the excitation light repeatedly, which enables more sensitive quantification than the conventional fluorometry.

Using such a system, quantification can be made for fluorescent derivatives of amines, drugs, steroids, and the like as well as amino acids.

According to the chemiluminescence assay of the present invention, highly sensitive and highly specific assay can be effected in combination with immunoassay. For example, quantification can be made by allowing an enzyme-labelled antigen and a standard antigen to competitively bind to an antibody, determining peroxide by chemiluminescence reaction, which is formed by the reaction between a substrate and the enzyme-labelled antigen, plotting chemiluminescence against the amount of the standard antigen (calibration curve) to calculate based on it.

EXAMPLE

In the following, Examples of the present invention is provided.

Example 1

A fluorescent group-containing carbodiimide compound of the present invention was synthesized in the following manner. This reaction is illustrated in the following reaction formula (1).

(1) Synthesis of thiourea compound

In 15 ml of dry methylene chloride was dissolved 1.4 g (10 mmol) of 3-(dimethylaminopropyl)isothiocyanate and the mixture was cooled in ice. After adding 1.4 g (10 mmol) of N-(3-aminopropyl)morpholine, the mixture was stirred overnight at room temperature. Water was added to the reaction mixture and subjected to extraction with methylene chloride (5 ml×3 times). After dried over anhydrous potassium carbonate, the resulting mixture was concentrated to obtain 2.7 g (yield: 98%) of N-[3-(dimethylamino)]propyl-N'-(3-morpholino)propylthiourea (Compound (1) in the following Reaction formula (1). NMR spectrum data of this compound are shown below.

$^1$H-NMR (CDCl$_3$): δ=1.70–1.80 (m, 4H), 2.24 (s, 6H), 2.40–2.50 (m, 8H), 3.30–3.70 (m, 4H), 3.73 (t, 4H), 6.6–9.5 (m, 2H).

(2) Synthesis of carbodiimide group-containing compound

In 35 ml of acetone was dissolved 2.7 g (10 mmol) of N-[3-(dimethylamino)]propyl-N'-(3-morpholino)propyl-thiourea (Compound (1)). Further, 4.2 g (20 mmol) of mercury oxide was added, and the resulting mixture was stirred for 2 hours under reflux. Then, the reaction mixture was allowed to cool and filtered. The solvent was distilled off to obtain a crude product. This product was evaporated under reduced pressure to obtain 1.5 g (yield: 60%) of N-[3-(dimethyl-amino)]propyl-N'-(3-morpholino)propyl-carbodiimide (Compound (2) in the following reaction formula (1)). Its boiling point (b.p.) was from 125° to 128° C./0.2 mmHg. NMR spectrum data of Compound (2) are shown below.

$^1$H-NMR (CDCl$_3$): δ=1.70–1.80 (m, 4H), 2.22 (s, 6H), 2.30–2.50 (m, 8H), 3.27 (t, 2H), 3.29 (t, 2H), 3.71 (t, 4H).

(3) Synthesis of fluorescent group-containing carbodiimide compound

N-[3-(dimethylamino)]propyl-N'-(3-morpholino)propyl-carbodiimide (Compound (2)) was dissolved in 10 ml of dry dimethylformamide, and 135 mg (0.5 mmol) of 4-bromomethyl-7-methoxycoumarin (Dojin Kagaku) was further added thereto, followed by stirring at room temperature over a day and a night. Then, dimethylformamide was distilled off under reduced pressure and the resulting pale yellow powder was dissolved in 3 ml of methanol. Diethylether was added thereto to reprecipitate and 250 mg (yield:

94%) of a fluorescent group-containing carbodiimide compound (Compound (3) in the following reaction formula (1)) was obtained. NMR spectrum data of this compound are shown below.

$^1$H-NMR (DMSO-d$_6$): δ=1.60–1.70 (m, 2H), 1.90–2.10 (m, 2H), 2.30–2.40 (m, 6H), 3.09 (s, 6H), 3.20–3.40 (m, 6H), 3.56 (t, 4H), 3.89 (s, 3H), 4.72 (s, 2H), 6.66 (s, 1H), 7.01 (dd, 1H), 7.10 (d, 1H), 8.13 (d, 1H).

(4) Synthesis of quaternary salt of fluorescent group-containing carbodiimide compound In 5 ml of dry dimethylformamide was dissolved 190 mg (0.3 mmol) of the fluorescent group-containing carbodiimide compound (Compound (3)). After adding 56 mg (0.3 mmol) of methyl p-toluenesulfonate, the resulting mixture was stirred at room temperature over a day and a night. Dimethyl-formamide was distilled off under reduced pressure, and the resulting pale yellow powder was dissolved in 3 ml of methanol. Diethylether was added thereto to reprecipitate and 230 mg (yield: 93%) of a quaternary salt of the fluorescent group-containing carbodiimide compound (Compound-1 in the following reaction formula (1)) was obtained. NMR spectrum data of this compound are shown below.

$^1$H-NMR (DMSO-d$_6$): δ=1.80–2.10 (m, 4H), 2.29 (s, 3H), 3.08 (s, 6H), 3.14 (s, 3H), 3.30–3.60 (m, 14H), 3.89 (s, 3H), 4.72 (s, 2H), 6.65 (s, 1H), 6.98 (dd, 1H), 7.10–7.13 (m, 3H), 7.49 (d, 2H), 8.12 (d, 1H).

REACTION FORMULA (1)

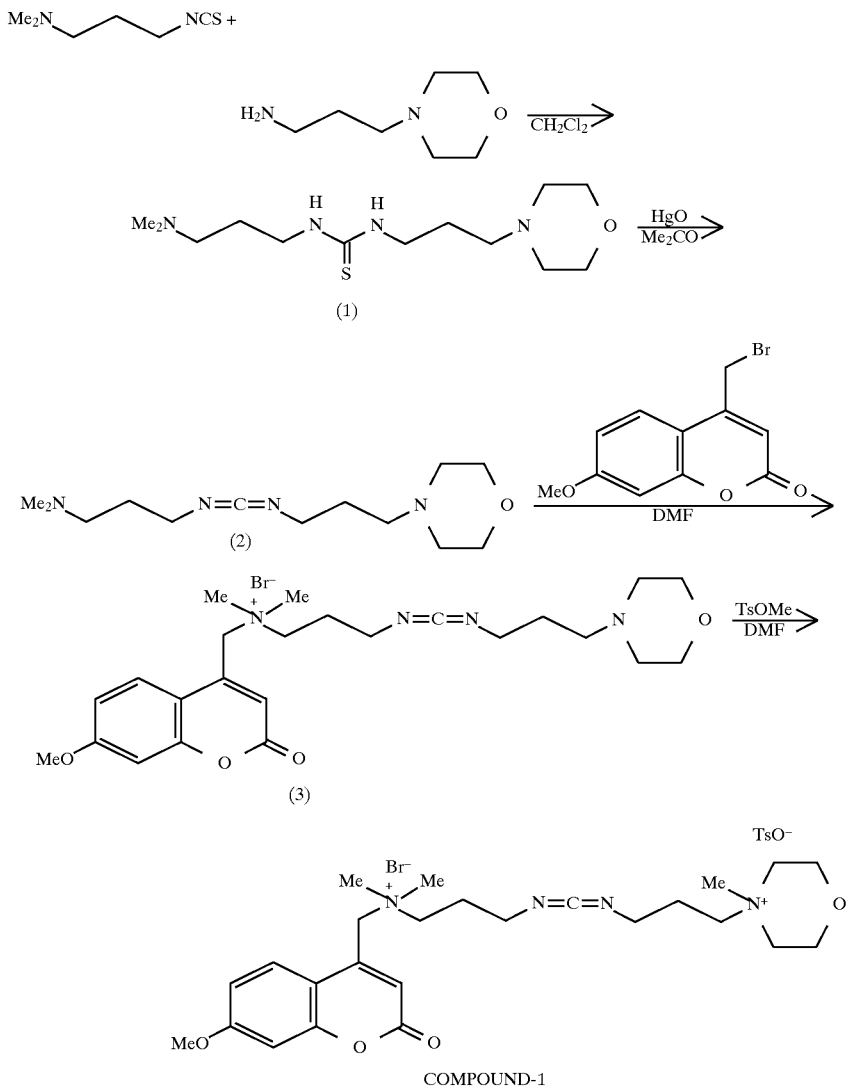

Example 2

A fluorescent group-containing carbodiimide compound of the present invention was synthesized in the following manner. This reaction is illustrated in the following reaction formula (2).

(1) Synthesis of fluorescent group-containing thiourea compound

First, 0.5 g (2.3 mmol) of 1-aminopyrene and 1.7 g (12 mmol) of 3-(dimethylamino)propylisothiocyanate were mixed and stirred at 120° C. for 30 minutes. After allowing the mixture to cool, 20 ml of ethyl acetate was added thereto and crystals thus precipitated were collected by filtration to obtain 0.5 g (yield: 54%) of a fluorescent group-containing thiourea compound (Compound (1) in the following Reaction formula (2)). NMR spectrum data of this compound are shown below.

$^1$H-NMR (CDCl$_3$): δ=0.82 (s, 6H), 1.40–1.50 (m, 2H), 1.90–2.00 (m, 2H), 3.68–3.73 (m, 2H), 7.90–8.20 (m, 8H), 8.70 (bs, 1H).

(2) Synthesis of fluorescent group-containing carbodiimide compound

In 25 ml of acetone was dissolved 0.2 g (0.55 mmol) of the fluorescent group-containing thiourea compound (Compound (1)). Further, 0.24 g (1.1 mmol) of mercury oxide was added, and the resulting mixture was stirred for 2 hours under reflux. The reaction mixture was allowed to cool and filtered to remove inorganic matters. Then, 0.24 g (1.1 mmol) of mercury oxide was further added to the filtrate, and the resulting mixture was stirred for 1.5 hours under reflux. After the reaction mixture was allowed to cool and filtered, the filtrate was concentrated and petroleum ether was added to the remaining viscous liquid to separate the petroleum ether layer. Petroleum ether was distilled off under reduced pressure to obtain the fluorescent group-containing carbodiimide (Compound (2) in the following reaction formula (2)). NMR spectrum data of this compound are shown below.

$^1$H-NMR (CDCl$_3$): δ=1.90–2.00 (m, 2H), 2.24 (s, 6H), 2.47 (t, 2H), 3.62 (t, 2H), 7.80–8.20 (m, 8H), 8.48 (d, 1H).

(3) Synthesis of quaternary salt of fluorescent group-containing carbodiimide compound In 2 ml of dry dimethylformamide was dissolved 100 mg (0.3 mmol) of the fluorescent group-containing carbodiimide compound (Compound (2)). After adding thereto 100 mg (0.6 mmol) of methyl p-toluenesulfonate, the resulting mixture was stirred at room temperature over a day and a night. Dimethylformamide was distilled off under reduced pressure, and the resulting pale yellow powder was dissolved in 2 ml of methanol. Diethylether was added thereto to reprecipitate and 130 mg (yield: 87%) of a quaternary salt of the fluorescent group-containing carbodiimide compound (Compound-2 in the following reaction formula (2)) was obtained. NMR spectrum data of this compound are shown below.

$^1$H-NMR (DMSO-d$_6$): δ=2.10–2.20 (m, 2H), 2.28 (s, 3H), 3.13 (s, 9H), 3.40–3.50 (m, 2H), 3.78 (t, 2H), 7.11 (d, 2H), 7.50 (d, 2H), 8.00–8.40 (m, 9H).

REACTION FORMULA (2)

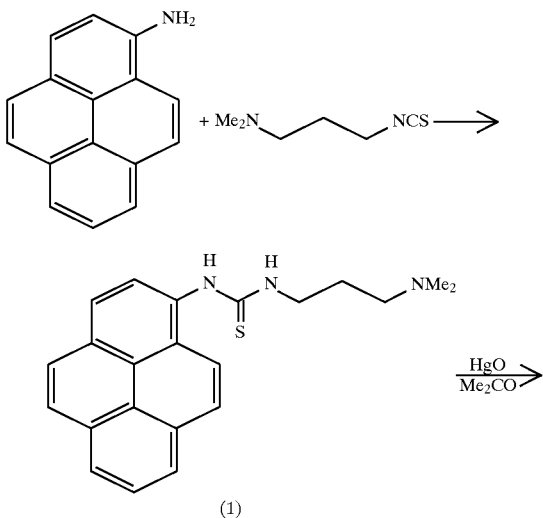

-continued
REACTION FORMULA (2)

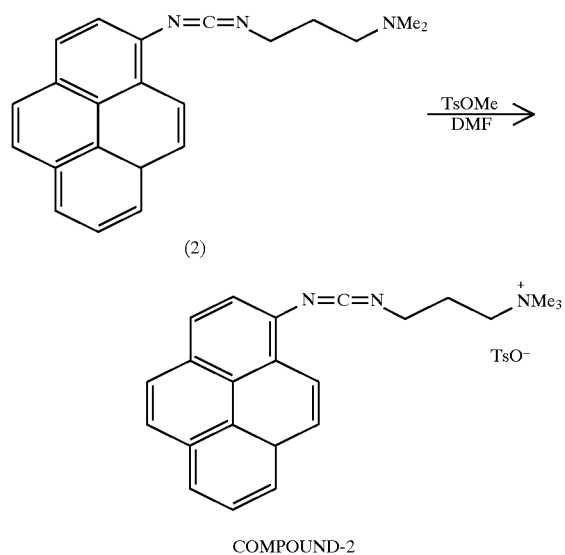

COMPOUND-2

Example 3

A fluorescent group-containing carbodiimide compound of the present invention was synthesized in the following manner. This reaction was shown in the following reaction formula (3).

(1) Synthesis of N-Fmoc-6-aminocaproic acid

In 50 ml of acetone was dissolved 1.31 g (10 mmol) of 6-aminocaproic acid. 50 ml of a solution of 0.84 g (10 mmol) of sodium hydrogencarbonate in water was added thereto. Then, 3.37 g (10 mmol) of 9-fluorenyl methylsuccinimidyl carbonate (Fmoc-Osu) was further added to the reaction mixture under stirring and allowed to react at room temperature for 5 hours. After acetone was distilled off under reduced pressure, methylene chloride was added to the reaction mixture for extraction. This extraction operation was repeated twice and the organic layer was washed with a saturated sodium chloride solution. After drying it over anhydrous magnesium sulfate, the solvent was distilled off to obtain 2.96 g (yield: 84%) of the desired N-Fmoc-6-aminocaproic acid (Compound (1) in the following reaction formula (3)). NMR spectrum data of this compound are shown below.

$^1$H-NMR (DMSO-d$_6$): δ=1.20–1.75 (m, 6H), 2.40 (t, 2H), 3.10–3.25 (m, 2H), 4.20 (t, 1H), 4.45 (d, 2H), 7.25–7.50 (m, 4H), 7.70 (d, 2H), 7.90 (d, 2H), 8.05–8.40 (m, 9H), 10.30 (s, 1H).

(2) Synthesis of amino group-containing fluorescent compound 10 ml of thionyl chloride was added to 1.06 g (3 mmol) of Compound (1) thus obtained to dissolve it, the mixture was allowed to react for 30 minutes under reflux. After allowing the mixture to cool to the room temperature, thionyl chloride was distilled off under reduced pressure. The residue was dissolved in 20 ml of methylene chloride and 0.52 ml (3 mmol) of ethyl diisopropylamine was added thereto. Twenty ml of a solution of 0.65 g (3 mmol) of 1-aminopyrene in dry methylene chloride was added dropwise to the reaction mixture. After completion of addition, the reaction mixture was stirred at room temperature for 18 hours. Water was added to the reaction mixture and extraction was carried out twice with methylene chloride. After drying the organic layer over anhydrous magnesium sulfate, the solvent was distilled off to obtain about 2.5 g of the reaction mixture. This reaction mixture was purified by silica gel column chromatography (developing solvent: chloroform/methanol=50/1) to obtain 0.89 g (yield: 54%) of Compound (2) in the following reaction formula (3). NMR spectrum data of this compound are shown below.

$^1$H-NMR (DMSO-d$_6$): δ=1.35–1.60 (m, 4H), 1.60–1.80 (m, 2H), 2.55 (t, 2H), 2.05 (t, 2H), 4.20–4.35 (m, 3H), 7.25–7.50 (m, 4H), 7.70 (d, 2H), 7.90 (d, 2H), 8.05–8.40 (m, 9H), 10.30 (s, 1H).

In 20% piperidine-containing dry dimethylformamide was dissolved 0.66 g (1.2 mmol) of Compound (2) thus obtained, followed by stirring at room temperature for 30 minutes. Then, the solvent was distilled off by heating under reduced pressure. Methylene chloride was added to the residue and stirred for a while. The insoluble matters were filtered off and the filtrate was concentrated. This procedure was repeated twice to obtain 0.38 g (yield: 95%) of the desired amino group-containing fluorescent compound (Compound (3) in the following reaction formula (3)). NMR spectrum data of this compound are shown below.

$^1$H-NMR (DMSO-d$_6$): δ=1.35–1.50 (bs, 4H), 1.70 (t, 2H), 2.55 (bs, 4H), 8.05–8.40 (m, 9H), 10.30 (s, 1H).

(3) Synthesis of fluorescent group-containing thiourea compound

In 10 ml of dry methylene chloride was dissolved 0.33 g (1.0 mmol) of Compound (3) thus obtained. Then, 0.16 g (1.1 mmol) of 3-(dimethylaminopropyl)isothiocyanate was added and stirred at room temperature for 3 hours. Water was added to the reaction mixture and extraction was carried out with methylene chloride three times. The organic layer was washed with a saturated sodium chloride solution and dried over anhydrous magnesium sulfate. Then, the solvent was distilled off to obtain about 0.5 g of the reaction mixture. The resulting reaction mixture was purified by silica gel column chromatography (developing solvent: chloroform/methanol=9/1–1/1) to obtain 0.38 g (yield: 80%) of the fluorescent group-containing thiourea compound (Compound (4) in the following reaction formula (3)). NMR spectrum data of this compound are shown below.

$^1$H-NMR (DMSO-d$_6$): δ=1.40–1.50 (m, 2H), 1.50–1.60 (m, 4H), 1.60–1.75 (m, 2H), 2.05 (s, 6H), 2.10 (t, 2H), 2.50 (bs, 2H), 7.50 (bs, 2H), 8.05–8.40 (m, 9H), 10.30 (s, 1H).

(4) Synthesis of fluorescent group-containing carbodiimide compound

In 10 ml of acetone was dissolved under heating 0.35 g (0.8 mmol) of Compound (4) thus obtained. Further, 0.35 g (1.6 mmol) of mercury oxide was added. The mixture was allowed to react for 4 hours under reflux and, then, cooled in ice, followed by filtration to remove the insoluble matters. After the filtrate was concentrated, petroleum ether was added and the insoluble matters were removed again by filtration. The filtrate was concentrated to obtain 0.32 g (yield: 90%) of the carbodiimide compound (Compound (5) in the following reaction formula (3)). NMR spectrum data of this compound are shown below.

$^1$H-NMR (CDCl$_3$-d$_6$): δ1.40–1.80 (m, 8H), 2.20 (s, 6H), 2.25 (t, 2H), 2.45 (t, 2H), 3.10–3.30 (m, 4H), 7.75–8.10 (m, 9H), 8.50 (s, 1H).

In 3 ml of dry dimethylformamide was dissolved 0.25 g (0.57 mmol) of Compound (5) thus obtained. Further, 0.18 ml (1.2 mmol) of methyl p-toluenesulfonate was added thereto to react overnight at room temperature. The solvent was distilled off under reduced pressure to the extent that the residue was not dried completely and diethyl ether was added to obtain 0.34 g (yield: 96%) of viscous yellow solid (fluorescent group-containing carbodiimide compound: Compound-3 in the following reaction formula (3)). NMR spectrum data of this compound are shown below.

$^1$H-NMR (DMSO-d$_6$): δ=1.40–1.85 (m, 8H), 2.55 (t, 2H), 3.05 (s, 9H), 3.05–3.10 (bs, 2H), 3.25–3.40 (m, 4H), 7.10 (d, 2H), 7.50 (d, 2H), 8.00–8.40 (m, 9H), 10.30 (s, 1H).

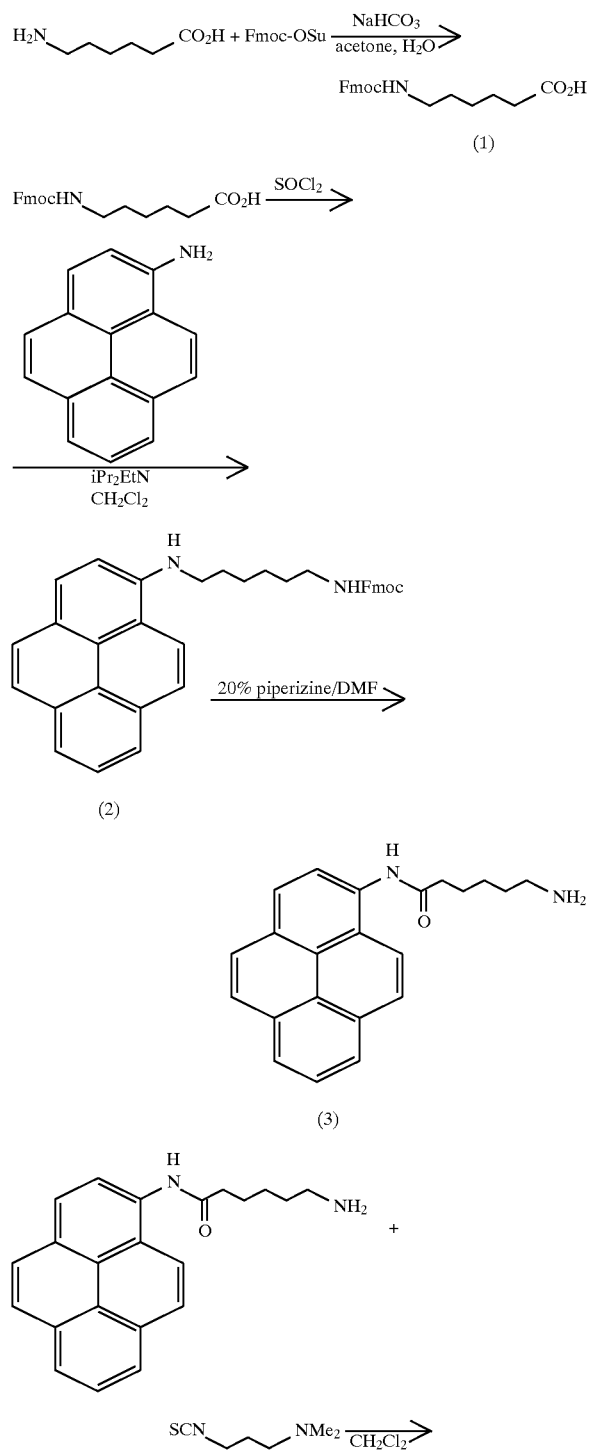

-continued
REACTION FORMULA (3)

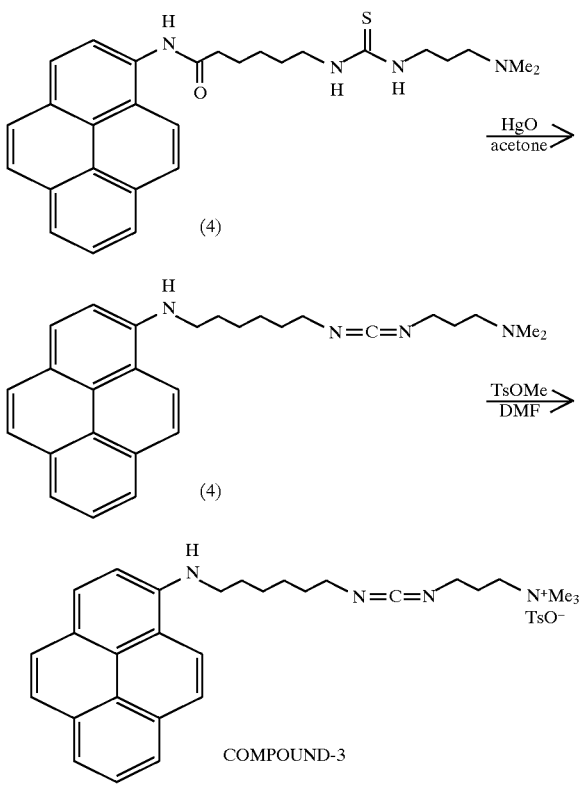

Example 4

A fluorescent group-containing carbodiimide compound of the present invention was synthesized in the following manner. This reaction was shown in the following reaction formula (4).

(1) Synthesis of thiourea compound

To 10 ml of dry methylene chloride was added 1.44 g (10 mmol) of 3-(dimethylaminopropyl)isothiocyanate. Further, 1.2 ml (10 mmol) of N,N-dimethyl-1,3-propanediamine was added under stirring at room temperature. The mixture was continuously stirred overnight at room temperature. Then, water was added to the reaction mixture, and extraction was carried out with methylene chloride three times. After dried over anhydrous magnesium sulfate, the mixture was concentrated to obtain 2.06 g (yield: 84%) of the desired thiourea compound (Compound (1) in the following reaction formula (4)). NMR spectrum data of this compound are shown below.

$^1$H-NMR (CDCl$_3$-d$_6$): ($\delta$=1.75 (t, 4H), 2.25 (s, 12H), 2.30 (t, 4H), 3.20–3.80 (bs, 4H), 8.00–9.40 (bs, 2H).

(2) Synthesis of carbodiimide group-containing compound

In 12 ml of acetone was dissolved 1.0 g (4 mmol) of Compound (1) thus obtained. Further, 1.73 g (8 mmol) of mercury oxide was added. After reaction for 3 hours under reflux, the reaction mixture was cooled in ice and the insoluble matters were removed by filtration. The reaction mixture was concentrated and petroleum ether was added thereto to remove the insoluble matters again by filtration. The filtrate was concentrated to obtain 0.75 g (yield: 89%) of the carbodiimide group-containing compound (Compound (2) in the following reaction formula (4)). NMR spectrum data of this compound are shown below.

$^1$H-NMR (CDCl$_3$-d$_6$): $\delta$=1.65–1.80 (m, 4H), 2.25 (s, 12H), 2.35 (t, 4H), 3.25 (t, 4H).

(3) Synthesis of fluorescent group-containing carbodiimide compound

In 5 ml of dry dimethylformamide was dissolved 0.2 g (1 mmol) of Compound (2) thus obtained. Further, 0.54 g (2 mmol) of 4-bromomethyl-7-methoxycoumarin was added thereto, followed by stirring at room temperature for 2 days. Dimethylformamide was distilled off under reduced pressure and the resulting yellow powder was dissolved in a small amount of methanol. Diethyl ether was added to reprecipitate it to obtain 0.69 g (yield: 92%) of the fluorescent group-containing carbodiimide compound (Compound-4 in the following reaction formula (4)). NMR spectrum data of this compound are shown below.

$^1$H-NMR (DMSO-d$_6$): $\delta$=2.00–2.10 (m, 4H), 3.10 (s, 12H), 3.35–3.40 (t, 4H), 3.55–3.70 (m, 4H), 3.90 (s, 6H), 4.80 (s, 4H), 6.70 (s, 2H), 7.00 (dd, 2H), 7.10 (d, 2H), 8.20 (d, 2H).

REACTION FORMULA (4)

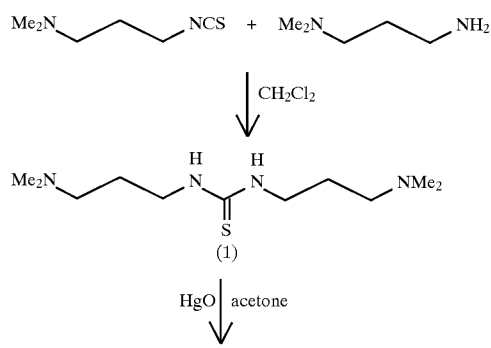

-continued
REACTION FORMULA (4)

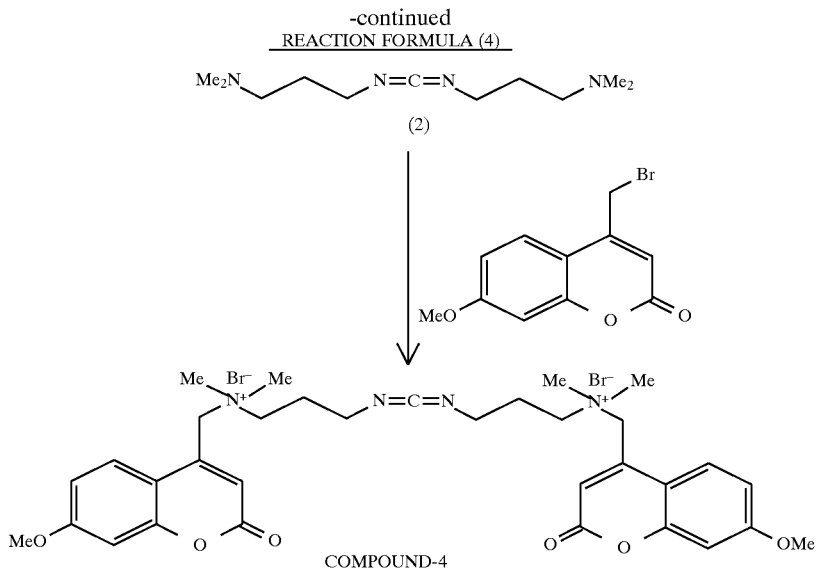

COMPOUND-4

Example 5

A fluorescent group-containing carbodiimide compound of the present invention (thiazole orange group-containing carbodiimide compound) was synthesized in the following manner. This reaction is shown in the following reaction formula (5). In the reaction formula (5), Et stands for an ethyl group.

(1) Synthesis of Compound (1) in the reaction formula (5)

To 3.0 ml (24 mmol) of 2-methylthiazole was added 3.6 ml (24 mmol) of methyl p-toluenesulfonate. The mixture was allowed to react at 160° C. for 1 hour. After cooling to room temperature, crystals thus formed were dissolved in a mixed solvent of chloroform and methanol. This solution was poured into a large volume of diethyl ether, and crystals thus precipitated were isolated by filtration to obtain 7.8 g of the desired compound (Compound (1) in the reaction formula (5)). NMR spectrum data of Compound (1) thus obtained are shown below.

$^1$H-NMR (DMSO-$d_6$): δ=3.05 (s, 3H), 4.10 (s, 3H), 6.95 (d, 2H), 7.35 (d, 2H), 7.70 (t, 1H), 7.75 (t, 1H), 8.15 (d, 1H), 8.35 (d, 1H).

(2) Synthesis of Compound (2) in the reaction formula (5)

To 1.0 g (6.1 mmol) of 4-chloroquinoline was added 5 ml (43 mmol) of 1,3-diiodopropane. The mixture was allowed to react 120 for 1 hour. After cooling to room temperature, crystals formed were added to chloroform to crush into powder and filtered under reduced pressure. The resulting crystals were washed with ethylene chloride and allowed to air-dry to obtained 2.4 g of the desired compound (Compound (2) in the reaction formula (5)). NMR spectrum data of Compound (2) thus obtained are shown below.

$^1$H-NMR (DMSO-$d_6$): δ=2.40–2.60 (m, 2H), 3.40 (t, 2H), 5.05 (t, 2H), 8.15 (t, 1H), 8.35 (t, 1H), 8.45 (d, 1H), 8.60 (d, 1H), 8.90 (d, 1H), 9.15 (d, 1H).

(3) Synthesis of Compound (3) in the reaction formula (5)

30 ml of methylene chloride was added to 1.0 g (3.0 mmol) of Compound (1) and 1.37 g (3.0 mmol) of Compound (2) to give a suspension and 0.42 ml (3.0 mmol) of triethylamine was added thereto. After allowing the mixture to react overnight, undissolved crystals were separated by filtration, and water was added to the filtrate, followed by stirring for a while. Crystals thus precipitated were isolated by filtration, and the crystals were dissolved in a mixed solvent of chloroform and methanol. This solution was poured into a large volume of diethyl ether, and crystals thus precipitated were separated by filtration to obtain 0.5 g of the desired compound (Compound (3) in the reaction formula (5)). NMR spectrum data of this compound are shown below.

$^1$H-NMR (DMSO-$d_6$): δ=2.30–2.50 (m, 2H), 4.00 (s, 3H), 4.65 (t, 2H), 6.90 (s, 1H), 7.35 (d, 1H), 7.40 (t, 1H), 7.60 (t, 1H), 7.70–7.80 (m, 2H), 7.95–8.15 (m, 3H), 8.60 (d, 1H), 8.80 (d, 1H).

(4) Synthesis of thiazole orange group-containing carbodiimide compound

In 7 ml of dimethylformamide was dissolved 0.20 g (0.34 mmol) of Compound (3). 3 ml of a solution of 0.20 g (1.4 mmol) of 1-ethyl-3-(3-dimethylaminopropyl)carbodiimide in dimethylformamide was added thereto and stirred overnight. After the solvent was distilled off under reduced pressure, the residue was redissolved in a small amount of dimethylformamide. This solution was poured into a large volume of diethyl ether, and crystals thus precipitated were separated by filtration to obtain 0.24 g of desired thiazole orange group-containing carbodiimide compound (Compound-5 in the reaction formula (5)). NMR spectrum data of this compound are shown below.

$^1$H-NMR (DMSO-$d_6$): δ=1.05 (t, 3H), 1.80–1.95 (m, 2H), 2.15–2.30 (m, 2H), 3.00 (s, 6H), 3.15 (q, 2H), 3.45–3.60 (m, 2H), 3.90 (s, 3H), 4.45–4.60 (m, 2H), 6.80 (s, 1H), 7.15 (d, 1H), 7.30 (t, 1H), 7.45 (t, 1H), 7.45–7.70 (m, 2H), 7.80–7.95 (m, 2H), 8.05 (d, 1H), 8.55 (d, 1H), 8.70 (d, 1H).

REACTION FORMULA (5)
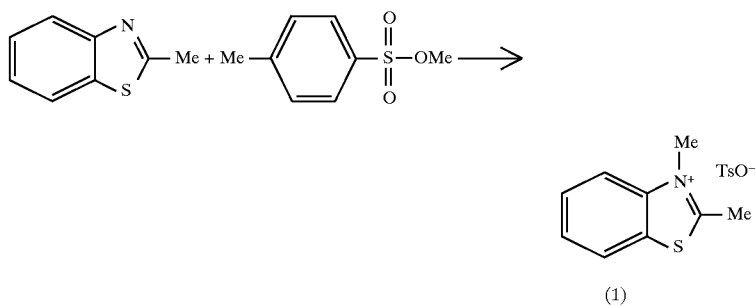
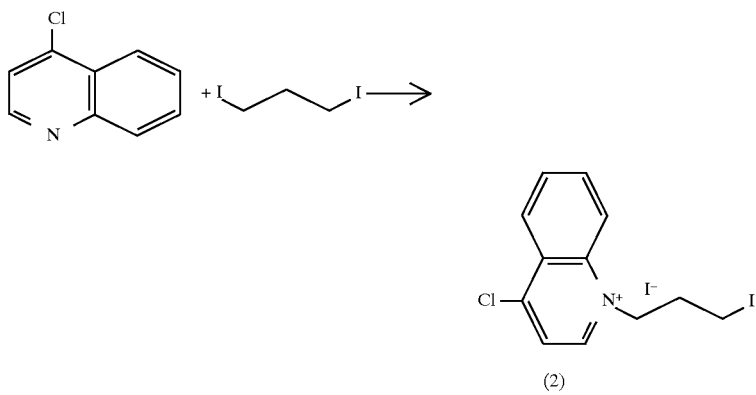
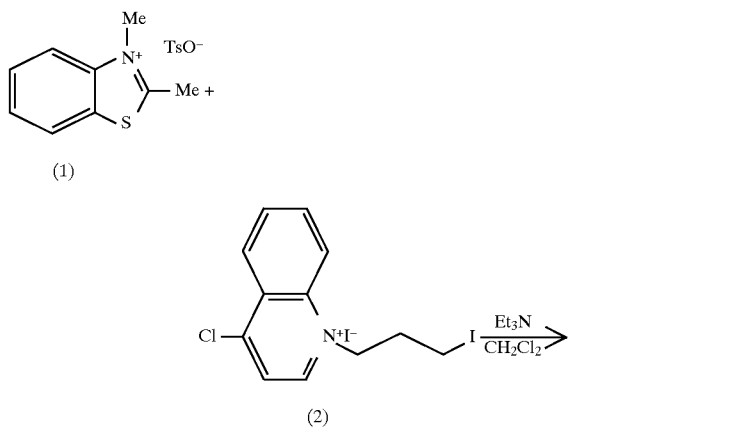
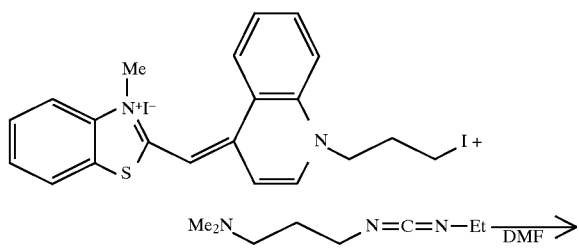

-continued
REACTION FORMULA (5)

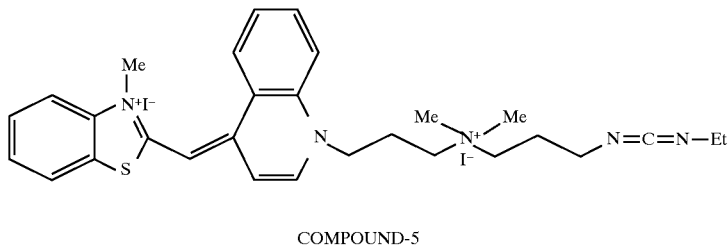

COMPOUND-5

Example 6

A fluorescent group-containing carbodiimide compound of the present invention (florescent rare earth metal chelate-containing carbodiimide compound) was synthesized in the following manner. This reaction is shown in the following reaction formula (6). In the reaction formula (6), Et stands for an ethyl group.

(1) Synthesis of 5-nitro-1,10-phenanthroline (Compound (1))

To 3.1 g (17 mmol) of 1,10-phenanthroline hydrate were added 0.84 ml of concentrated sulfuric acid and 3.6 ml of fuming sulfuric acid to dissolve the compound by heating. After the temperature of the solution was adjusted to 170° C., 8.2 ml of concentrated nitric acid was added dropwise thereto, and the mixture was stirred overnight at 170° C. The resulting solution was adjusted to pH 3 with an aqueous solution of sodium hydroxide, and precipitate thus formed was filtered to obtain 1.49 g (42%) of Compound (1) as a yellow solid.

$^1$H-NMR (CDCl$_3$): δ=7.75–7.85 (m, 2H), 8.43 (d, 1H), 8.68 (s, 1H), 9.02 (d, 1H), 9.30 (d, 1H), 9.35 (d, 1H)

(2) Synthesis of 5-amino-1,10-phenanthroline (Compound (2))

In 3.0 ml of acetic acid was dissolved 1.37 g (5.8 mmol) of 5-nitro-1,10-phenanthroline. A solution prepared by dissolving 1.08 g (4.8 mmol) of stannic chloride (II) dihydrate in 2.2 ml of concentrated hydrochloric acid was added dropwise thereto, followed by stirring at 100° C. for 2 hours. The reaction mixture was made alkaline with a NaOH aqueous solution and extracted with chloroform. After chloroform was distilled off under reduced pressure, a yellow solid was obtained. This was recrystallized from tetrahydrofurane-hexane to obtain 0.75 g (66%) of the desired 5-amino-1,10-phenanthroline (Compound (2)).

$^1$H-NMR (CDCl$_3$): δ=6.95 (s, 1H), 7.50 (m, 1H), 7.65 (m, 1H), 7.98 (d, 1H), 8.28 (d, 1H), 8.95 (d, 1H), 9.20 (d, 1H).

(3) Synthesis of Compound (3)

13 ml of thionyl chloride was added to 0.54 g (2.8 mmol) of 6-bromohexanoic acid and stirred at room temperature for 4 hours. Thionyl chloride was distilled off under reduced pressure to obtain a transparent liquid. 5 ml of methylene chloride was added thereto. The thus prepared solution was added to 25 ml of methylen chloride solution of 0.33 g (1.7 mmol) of 5-amino-1,10-phenanathroline and 0.45 ml (3.3 mmol) of triethylamine under atmosphere of argon and the mixture was stirred at room temperature for 4 hours. Then, 20 ml of distilled water was added to the reaction mixture to carry out extraction, the organic layer was washed with saturated sodium hydrogencarbonate solution and saturated sodium chloride solution, and dried over magnesium sulfate. After filtration, the solvent was distilled off under reduced pressure to obtain an oily fraction. This was purified by silica gel column chromatography (chloroform-methanol system) to obtain 0.53 g (84%) of the desired Compound (3).

$^1$H-NMR (CDCl$_3$): δ=1.36–1.44 (m, 2H), 1.63–1.70 (m, 2H), 1.73–1.80 (m, 2H), 2.43 (t, 2H), 3.33 (t, 2H), 7.28–7.32 (m, 1H), 7.37–7.42 (m, 1H), 7.70 (s, 1H), 7.84 (d, 1H), 8.31 (d, 1H), 8.87 (s, 1H), 9.44 (s, 1H).

(4) Synthesis of Compound (4)

2 g (37 mmol) of sodium methoxide was added to 10 ml of dry ether and 1.5 g (10 mmol) of ethyl trifluoroacetate was added dropwise thereto. Then, 1.3 g (10 mmol) of 2-acetylthiophene was added and stirred for 12 hours. After the solvent was distilled off, the residue was dried, 9.3 ml of 10% sulfuric acid was added and stirred to precipitate the desired product. Crystals were separated by filtration, and subjected to recrystallization from ethanol twice to obtain 1.1 g (49%) of colorless needle crystals of 2-thenoyltrifluoroacetone.

$^1$H-NMR (CDCl$_3$): δ=6.45 (s, 2H), 7.20 (t, 1H), 7.75 (d, 1H), 7.83 (d, 1H).

20 ml of 95% ethanol was added to 0.67 g (3 mmol) of 2-thenoyltrifluoroacetone and 0.37 g (1 mmol) of Compound (3) to dissolve by heating. Then, 3 ml of 1N aqueous solution of sodium hydroxide was added for neutralization. 10 ml of aqueous solution of 0.37 g (1 mmol) of europium chloride hexahydrate was added to the above solution with heating at about 60° C. After cooling, the purified complex was separated and washed with water containing a small amount of ethanol several times. Thereafter, this solution was dissolved in a mixed solvent of ethanol and acetone under heating. The resulting solution was filtered, and the solvent was concentrated to about ⅕ of the starting amount. After allowing the resulting concentrate to stand overnight, crystals precipitated were separated by filtration, washed with ethanol aqueous solution, dried, and allowed to stand in a desiccator containing phosphorus pentoxide for one day, to thereby obtain 0.76 g (64%) of the desired Compound (4).

$^1$H-NMR (CDCl$_3$): δ=1.36–1.44 (m, 2H), 1.63–1.70 (m, 2H), 1.73–1.80 (m, 2H), 2.43 (t, 2H), 3.33 (t, 2H), 3.42 (s, 3H), 7.22 (t, 3H), 7.80 (d, 3H), 7.88 (d, 3H), 8.43–8.47 (m, 1H), 8.57–8.62 (m, 1H), 8.90 (s, 1H), 9.05 (d, 1H), 9.50 (d, 1H), 10.28 (s, 1H), 10.40 (s, 1H).

(5) Synthesis of florescent rare earth metal chelate-containing carbodiimide compound (Compound-6)

In 10 ml of dimethylformamide was dissolved 0.48 g (0.4 mmol) of Compound (4). 1 ml of dimethylformamide solution of 0.10 g (0.7 mmol) of 1-ethyl-3-(3-dimethylaminopropyl)carbodiimide was added thereto and stirred overnight. After the solvent was distilled off under reduced pressure, the residue was redissolved in a small amount of dimethylformamide. This solution was poured into a large volume of diethyl ether, and crystals precipitated were separated by filtration to obtain 0.43 g (80%) of the desired florescent rare earth metal chelate-containing carbodiimide compound (Compound-6 in the following reaction formula (6)).

$^1$H-NMR (CDCl$_3$): δ=1.10 (t, 3H), 1.36–1.44 (m, 2H), 1.63–1.70 (m, 2H), 1.73–1.80 (m, 2H), 1.90–2.00 (m, 2H), 2.43 (t, 2H), 3.20–3.60 (m, 17H), 7.22 (t, 3H), 7.80 (d, 3H), 7.88 (d, 3H), 8.43–8.47 (m, 1H), 8.57–8.62 (m, 1H), 8.90 (s, 1H), 9.05 (d, 1H), 9.50 (d, 1H), 10.28 (s, 1H), 10.40 (s, 1H).

(1) Synthesis of Compound (1)

In 10 ml of methylene chloride was dissolved 1.0 g (3.7 mmol) of dansyl chloride. Then, 0.47 g (4.0 mmol) of 1-aminohexanol was added thereto, followed by stirring. Further, 0.70 ml (4.0 mmol) of ethyl diisopropylamine was added thereto, followed by stirring at room temperature for

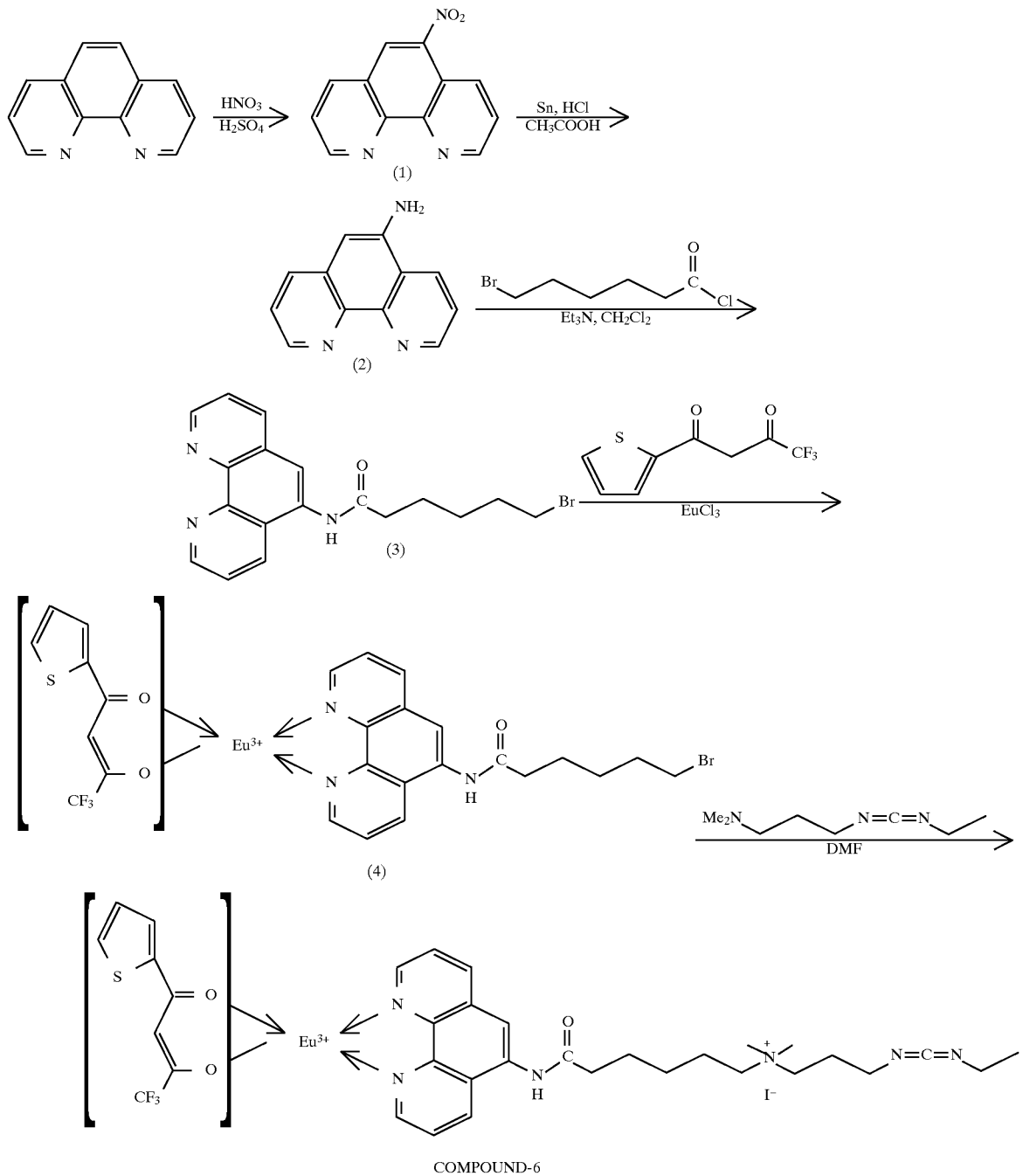

REACTION FORMULA (6)

COMPOUND-6

Example 7

A fluorescent group-containing carbodiimide compound of the present invention was synthesized in the following manner. This reaction was shown in the following reaction formula (7).

20 minutes. Then, water was added to the reaction mixture, and the organic layer was separated and dried over potassium carbonate. After filtration, the solvent was distilled off under reduced pressure, and the resulting reaction mixture was purified by silica gel column chromatography to obtain 1.40 g of Compound (1). NMR spectrum data of this compound are shown below.

$^1$H-NMR (CDCl$_3$): δ=1.05–1.25 (m, 4H), 1.25–1.45 (m, 4H), 2.30 (s, 1H), 2.80 (s, 6H), 2.80 (t, 2H), 3.30 (t, 2H), 5.40 (t, 1H), 7.10 (d, 1H), 7.55 (dd, 2H), 8.20 (d, 1H), 8.35 (d, 1H), 8.55 (d, 1H).

(2) Synthesis of Compound (2)

In 10 ml of dimethylformamide was dissolved 0.22 g (0.6 mmol) of Compound (1). Further, 0.9 g (2.0 mmol) of methyl triphenoxyphosphonium iodide was added thereto, and the resulting mixture was stirred overnight with the container protected from light. Then, 5 ml of methanol was added thereto, followed by stirring for 10 minutes, and the solvent was distilled off under reduced pressure. The residue was purified by silica gel column chromatography to obtain 0.12 g of Compound (2).

$^1$H-NMR (CDCl$_3$): δ=1.05–1.25 (m, 4H), 1.35 (t, 2H), 1.60 (t, 2H), 2.90 (s, 6H), 2.90 (t, 2H), 3.05 (t, 2H), 4.95 (t, 1H), 7.10 (d, 1H), 7.55 (dd, 2H), 8.25 (d, 1H), 8.35 (d, 1H), 8.55 (d, 1H).

(3) Synthesis of Compound-7

In 5 ml of dimethylformamide was dissolved 0.11 g (0.24 mmol) of Compound (2). Further, 0.10 g (0.64 mmol) of 1-ethyl-3-(3-dimethylaminopropyl)carbodiimide was added thereto, followed by stirring overnight. The solvent was distilled off under reduced pressure, and the residue was dissolved in a small amount of methylene chloride to add dropwise slowly into a large volume of hexane. The crystals thus precipitated were separated by filtration and dried to obtain 0.11 g of Compound-7 which is the desired product.

$^1$H-NMR (CDCl$_3$): δ=1.10 (t, 3H), 1.10–1.55 (m, 6H), 1.70 (t, 2H), 1.95 (t, 2H), 2.85 (s, 6H), 3.10–3.60 (m, 16H), 6.40 (t, 1H), 7.20 (d, 1H), 7.55 (dd, 2H), 8.20 (d, 1H), 8.40 (d, 1H), 8.50 (d, 1H).

REACTION FORMULA (7)

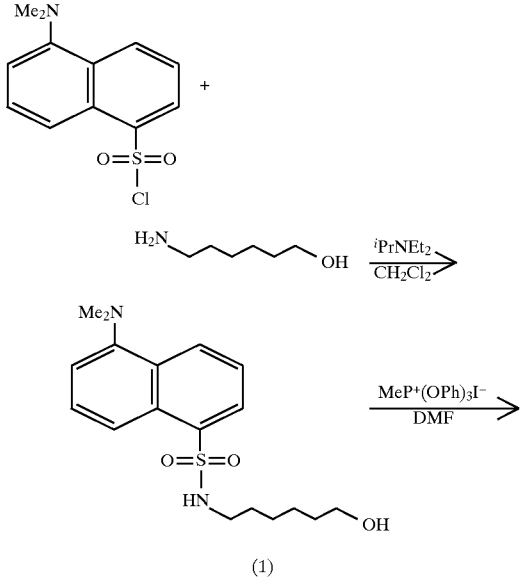

-continued
REACTION FORMULA (7)

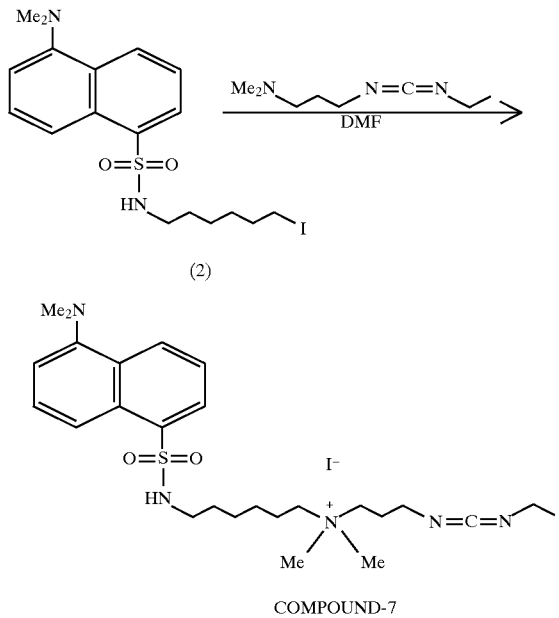

COMPOUND-7

Example 8

A fluorescent group-containing carbodiimide compound of the present invention was synthesized in the following manner. This reaction was shown in the following reaction formula (8).

(1) Synthesis of Compound (1)

In 50 ml of methanol was dissolved 5.0 g (33 mmol) of 2-mercaptooxazole. Further, 10 ml of methyl iodide and 4.56 g (33 mmol) of potassium carbonate were added thereto, followed by stirring at room temperature for 2 hours and a half. Then, methylene chloride and water were added to the reaction mixture, and the resulting mixture was extracted with methylene chloride. The organic layer was dried over potassium carbonate and filtered, and the solvent was distilled off under reduced pressure to obtain 5.27 g of Compound (1).

$^1$H-NMR (CDCl$_3$): δ=2.75 (s, 3H), 7.20 (t, 1H), 7.25 (t, 1H), 7.45 (d, 1H), 7.60 (d, 1H).

(2) Synthesis of Compound (2)

To 5.27 g (32 mmol) of Compound (1) was added 4.8 ml of methyl p-toluenesulfonate, followed by heating to 150° C. and stirring for 5 hours. After allowing the mixture to cool to room temperature, methanol was added to the caking reaction mixture to crush finely, and the solid was separated by filtration. The solid obtained was dissolved in a mixed solvent of methanol and methylene chloride, and crystallized by adding diethyl ether. The resulting crystals were separated by filtration and dried to obtain 5.0 g of Compound (2).

$^1$H-NMR (CDCl$_3$): δ=2.25 (s, 3H), 3.05 (s, 3H), 3.95 (s, 3H), 7.10 (d, 2H), 7.45 (d, 2H), 7.60–7.75 (m, 2H), 8.00–8.10 (m, 2H).

(3) Synthesis of Compound (3)

To 1.0 g (7.0 mmol) of 4-methylquinoline was added 5 ml of propyl 1,3-diiodide, followed by stirring at 120° C. for 1 hour. After allowing the mixture to cool to room temperature, 20 ml of ethyl acetate was added to the caking reaction mixture, followed by stirring for a while, and the supernatant was removed. Chloroform was added to the residue, followed by stirring for a while, to dissolve once. Further stirring for 1 hour formed yellow crystals. Ethyl acetate was added thereto, followed by stirring for a while, and the crystals were separated by filtration and dried to obtain 2.74 g of Compound (3).

$^1$H-NMR (DMSO-d$_6$): δ=2.50 (t, 2H), 3.00 (s, 3H), 3.30 (s, 3H), 3.35 (t, 2H), 5.00 (t, 2H), 8.05 (m, 2H), 8.25 (t, 1H), 8.60 (t, 2H), 9.35 (d, 1H).

(4) Synthesis of Compound (4)

In 8 ml of methylene chloride were dissolved 1.0 g (2.8 mmol) of Compound (2) and 1.3 g (3.0 mmol) of Compound (3), and 0.4 ml (2.8 mmol) of triethylamine was added thereto, followed by stirring at room temperature overnight. Methanol was added to the reaction mixture, followed by stirring for a while, and the residual crystals were separated by filtration to obtain 0.91 g of Compound (4) as orange crystals.

$^1$H-NMR (DMSO-d$_5$): δ=2.40 (t, 2H), 3.35 (s, 3H), 3.35 (t, 2H), 3.95 (s, 3H), 4.60 (t, 2H), 6.25 (s, 1H), 7.35–8.10 (m, 8H), 8.40 (d, 1H), 8.75 (d, 1H).

(5) Synthesis of Compound-8

To 20 ml of a dimethylformamide solution of 0.17 g (1.1 mmol) of 1-ethyl-3-(3-dimethylaminopropyl)carbodiimide was added 0.50 g (0.9 mmol) of Compound (4), followed by stirring overnight. The solvent was distilled off under reduced pressure, and the residue was redissolved in a small amount of dimethylformamide. This solution was poured into a large volume of diethyl ether, and the crystals thus precipitated were separated by filtration to obtain 0.36 g of Compound-8 which is the desired product.

$^1$H-NMR (DMSO-d$_6$): δ=1.15 (t, 2H), 1.95 (t, 2H), 2.30 (t, 2H), 3.05 (s, 6H), 3.25 (q, 2H), 3.30–3.40 (m, 4H), 3.45–3.60 (m, 2H), 3.90 (s, 3H), 6.30 (s, 1H), 7.40–8.20 (m, 8H), 8.45 (d, 1H), 8.80 (d, 1H).

REACTION FORMULA (8)

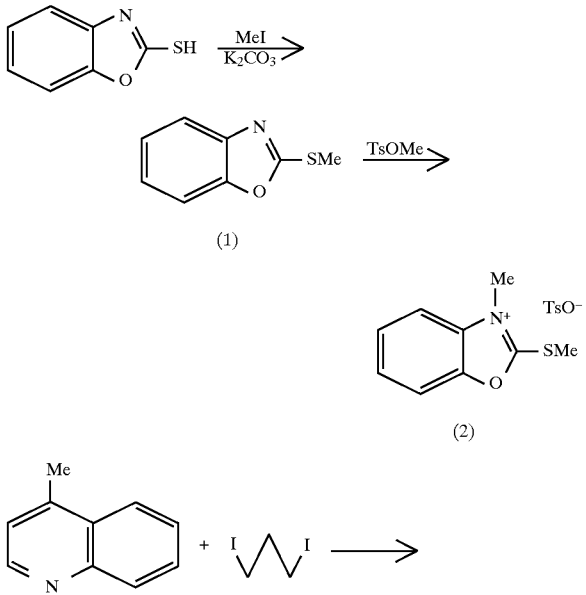

-continued
REACTION FORMULA (8)

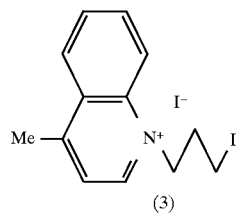

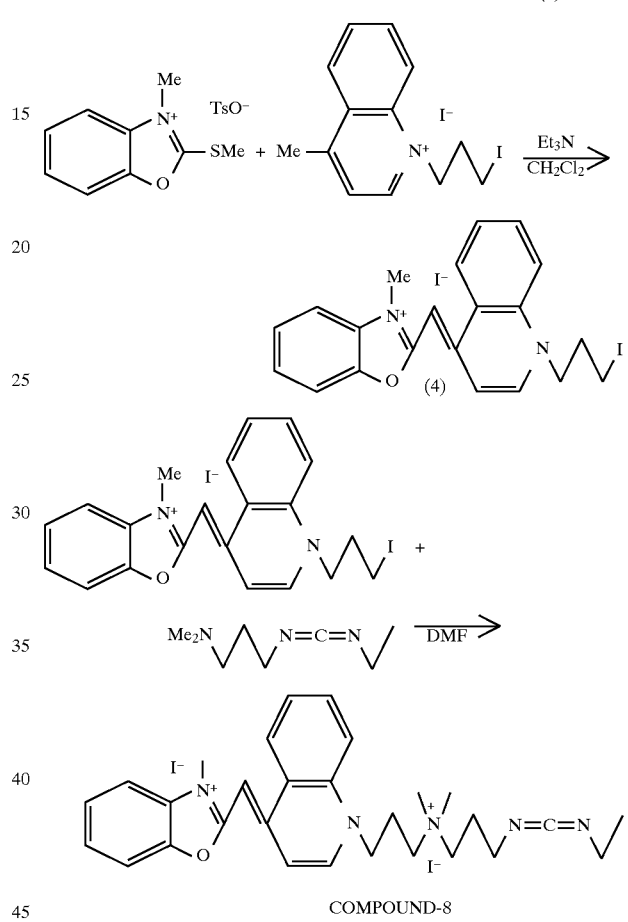

COMPOUND-8

Example 9

A fluorescent group-containing carbodiimide compound of the present invention was synthesized in the following manner. This reaction was shown in the following reaction formula (9).

(1) Synthesis of Compound (2)

In 20 ml of dimethylformamide was dissolved 0.26 g (0.8 mmol) of Compound (1), which is 4-(5,6-dimethoxybenzothiazolyl)benzoic acid. Further, 0.12 ml (0.9 mmol) of isobutyl chloroformate and 0.16 ml (0.9 mmol) of ethyl diisopropylamine were added thereto, followed by stirring at room temperature for 1 hour. Then, 0.10 g (0.9 mmol) of 6-aminohexanol was added thereto, followed by stirring for 1 hour and a half. The solvent was distilled off under reduced pressure, and the residue was purified by silica gel column chromatography to obtain 0.15 g of Compound (2).

$^1$H-NMR (DMSO-d$_6$): δ=1.25–1.60 (m, 8H), 3.25–3.45 (m, 4H), 3.89 (s, 3H), 3.90 (s, 3H), 4.40 (t, 1H), 7.60 (s, 1H), 7.70 (s, 1H), 8.00 (d, 2H), 8.10 (d, 2H), 8.60 (t, 1H).

(2) Synthesis of Compound (3)

In 5 ml of dimethylformamide was dissolved 0.12 g (0.3 mmol) of Compound (2). Further, 0.25 g (0.6 mmol) of methyl triphenoxyphosphonium iodide was added thereto, and the resulting mixture was stirred overnight with the container protected from light. Then, 5 ml of methanol was added thereto, followed by stirring for 10 minutes, and the solvent was distilled off under reduced pressure. The residue was purified by silica gel column chromatography to obtain 0.13 g of Compound (3).

$^1$H-NMR (CDCl$_3$): δ=1.35–1.55 (m, 4H), 1.60–1.75 (m, 2H), 1.80–1.95 (m, 2H), 3.20 (t, 2H), 3.45 (q, 2H), 3.95 (s, 6H), 6.25 (t, 1H), 7.35 (s, 1H), 7.55 (s, 1H), 7.85 (d, 2H), 8.05 (d, 2H).

(3) Synthesis of Compound-9

To 3 ml of a dimethylformamide solution of 0.04 g (0.25 mmol) of 1-ethyl-3-(3-dimethylaminopropyl) carbodiimide was added 0.10 g (0.2 mmol) of Compound (3), followed by stirring overnight. The solvent was distilled off under reduced pressure, and the residue was redissolved in a small amount of dimethylformamide. This solution was poured into a large volume of diethyl ether, and the crystals thus precipitated were separated by filtration to obtain 0.05 g of Compound-9 which is the desired product.

$^1$H-NMR (CDCl$_3$): δ=1.20 (t, 3H), 1.30–2.00 (m, 10H), 3.25 (q, 2H), 3.30 (s, 26H), 3.40–3.60 (m, 8H), 3.92 (s, 3H), 3.95 (s, 3H), 7.20 (s, 1H), 7.45 (s, 1H), 7.55 (t, 1H), 8.05 (dd, 4H).

distilled off under reduced pressure, and the residue was purified by silica gel column chromatography to obtain 0.05 g of Compound (1).

$^1$H-NMR (CDCl$_3$): δ=1.20–1.60 (m, 8H), 2.10 (s, 1H), 2.25 (s, 3H), 2.55 (s, 3H), 2.60 (t, 2H), 3.10–3.30 (m, 4H), 3.60 (t, 2H), 5.95 (bs, 1H), 6.10 (s, 1H), 6.30 (d, 1H), 6.90 (d, 1H), 7.10 (s, 1H).

(2) Synthesis of Compound (2)

In 2 ml of dimethylformamide was dissolved 0.05 g (0.13 mmol) of Compound (1). Further, 0.12 g (0.28 mmol) of methyl triphenoxyphosphonium iodide was added thereto, and the resulting mixture was stirred overnight with the container protected from light. Then, 1 ml of methanol was added thereto, followed by stirring for 10 minutes, and the solvent was distilled off under reduced pressure. The residue was purified by silica gel column chromatography to obtain 0.05 g of Compound (2).

$^1$H-NMR (CDCl$_3$): δ=1.20–1.50 (m, 6H), 1.70–1.80 (m, 2H), 2.25 (s, 3H), 2.55 (s, 3H), 2.60 (t, 3H), 3.10–3.30 (m, 6H), 5.75 (bs, 1H), 6.15 (s, 1H), 6.35 (d, 1H), 6.90 (d, 1H), 7.10 (s, 1H).

(3) Synthesis of Compound-10

To 0.04 g (0.25 mmol) of 1-ethyl-3-(3-dimethylaminopropyl)carbodiimide was added 3 ml of a dimethylformamide solution of 0.05 g (0.1 mmol) of Compound (2), followed by stirring overnight. The solvent was distilled off under reduced pressure, and the residue was redissolved in a small amount of dimethylformamide. This

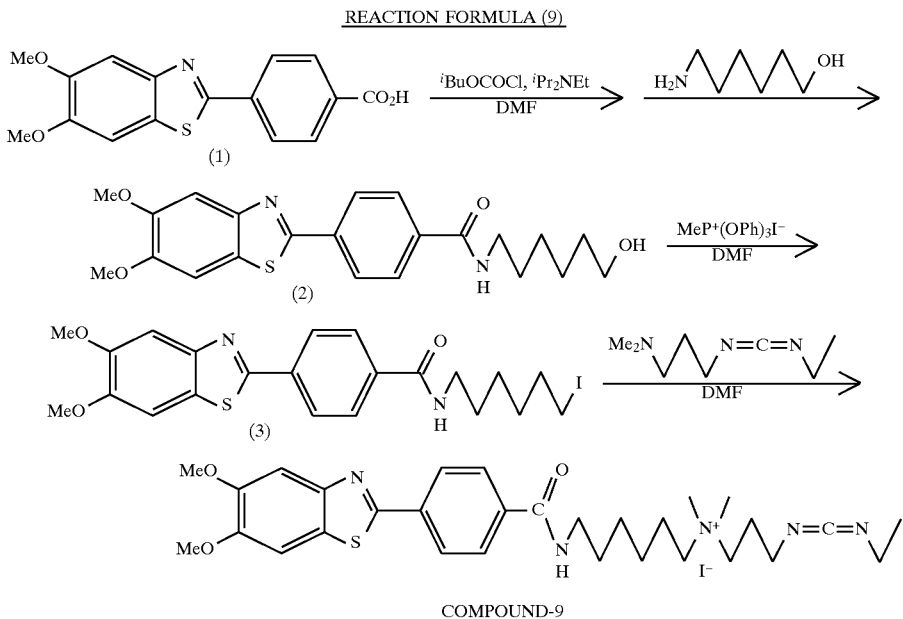

COMPOUND-9

Example 10

A fluorescent group-containing carbodiimide compound of the present invention was synthesized in the following manner. This reaction was shown in the following reaction formula (10).

(1) Synthesis of Compound (1)

To 1 ml of a methylene chloride solution of 0.05 g (0.13 mmol) of commercial BODIPY FL C$_3$-SE (Funakoshi Co.) was added 0.02 g (0.17 mmol) of 5-aminohexanol, followed by stirring at room temperature for 1 hour. The solvent was solution was poured into a large volume of diethyl ether, and the crystals thus precipitated were separated by filtration to obtain 0.04 g of Compound-10 which is the desired product.

$^1$H-NMR (CDCl$_3$): δ=1.20 (t, 3H), 1.20–1.50 (m, 6H), 1.70–1.80 (m, 2H), 1.80–2.05 (m, 4H), 2.25 (s, 3H), 2.55 (s, 3H), 2.65 (t, 3H), 3.10–3.30 (m, 10H), 3.40–3.60 (m, 6H), 6.10 (s, 1H), 6.35 (d, 1H), 6.60 (t, 1H), 6.90 (d, 1H), 7.20 (s, 1H).

REACTION FORMULA (10)

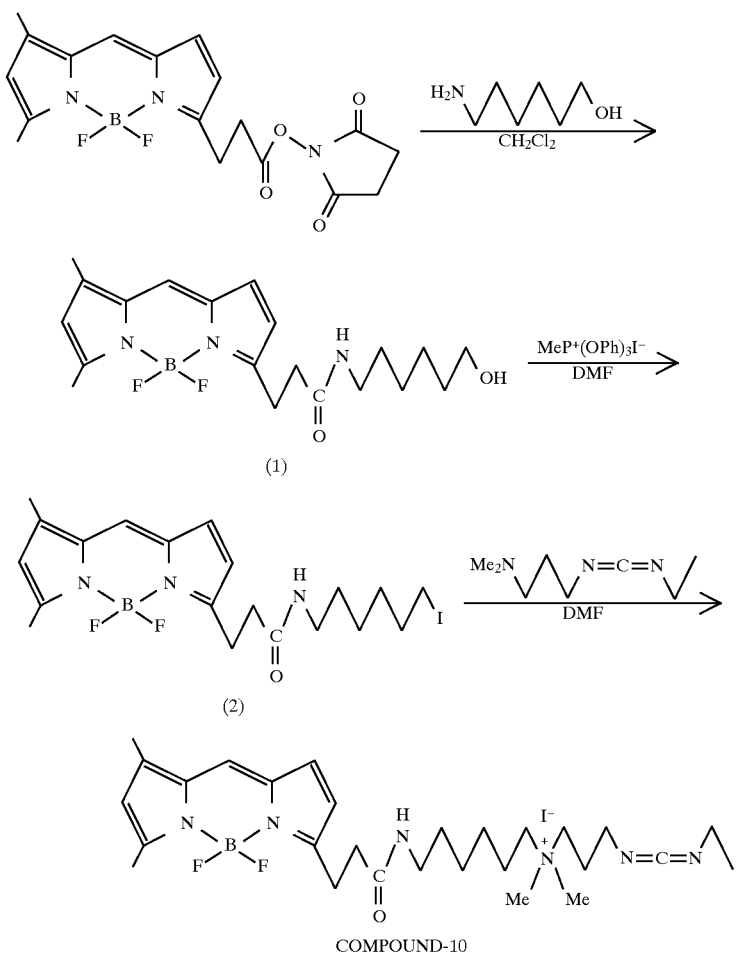

Example 11

(1) Synthesis of Compound-11

To 0.10 g (0.6 mmol) of 1-ethyl-3-(3-dimethylaminopropyl)carbodiimide was added 5 ml of a dimethylformamide solution of 0.17 g (0.4 mmol) of a commercial IANBD ester (Funakoshi Co.), and the resulting mixture was stirred overnight with the container protected from light. The solvent was distilled off under reduced pressure, and the residue was redissolved in a small amount of dimethylformamide. This solution was poured into a large volume of diethyl ether, and the crystals thus precipitated were separated by filtration to obtain 0.04 g of Compound-11 which is the desired product.

$^1$H-NMR (DMSO-d$_6$): δ=1.20 (t, 3H), 1.80–1.95 (m, 2H), 3.15 (s, 6H), 3.20–3.60 (m, 9H), 4.35 (s, 2H), 4.40–4.60 (m, 4H), 6.50 (d, 1H), 8.50 (d, 1H).

A fluorescent group-containing carbodiimide compound of the present invention was synthesized in the following manner. This reaction was shown in the following reaction formula (11).

REACTION FORMULA (11)

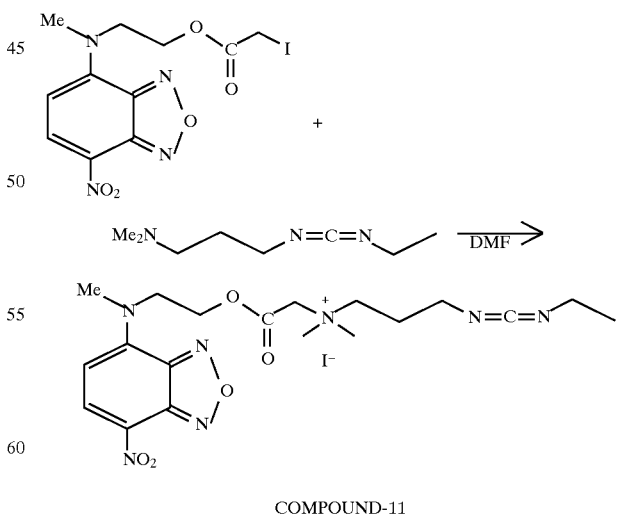

Example 12

Using Compound-1 to Compound-11 synthesized in Example 1–11, DNA was labelled with fluorescence by introducing a florescent group to DNA to obtain a fluorescence-labelled DNA-1 to fluorescence-labelled DNA-11 by the following method.

First of all, the reaction mixture (phage DNA (replicative form of M13mp18: Takara Shuzo) 1 pg; 0.1M borate buffer (pH 8.5); and 0.1M fluorescent group-containing carbodiimide compound) was incubated at 85° C. for 1 minute. Then, in order to remove the unreacted carbodiimide compound, the reaction mixture was mixed with 3M sodium acetate in a ⅕ amount of the sample and cold ethanol in a 2.5-fold amount of the sample, and the resulting mixture was allowed to stand at −80° C. for 45 minutes. The mixture was centrifuged at 4° C. at 12,000 rpm for 15 minutes using a centrifuge (H-1500FR Model, Kokusansha) to remove the upper layer. Then, 500 µl of 70% ethanol was added to the residue, and centrifugation was further carried out at 4° C. at 12,000 rpm for 1 minute and 30 seconds. After removing the upper layer, the precipitate was dissolved in 100 µl of sterilized water, and the mixture was kept at −20° C.

Example 13

Using the fluorescence-labelled DNA-1 tp fluorescence-labelled DNA-11 obtained in Example 12, hybridization was carried out by a microtiter plate method in the following manner.

(1) Immobilization of nucleic acid on the plate

Serial decimal dilutions of phage DNA (replicative form of M13mp18) linearized with a restriction enzyme (HindIII) was prepared using 2M NaCl so as to give 480 ng–4.8 pg/100 µl. The dilutions were heat-treated at 100° C. for 10 minutes and then quenched on ice for 5 minutes to obtain heat-denatured nucleic acid. The thus obtained heat-denatured nucleic acid in various concentrations was added to each well of the black microtiter plate for luminescence and coloring (Sumitomo bakelite Co.) and the plate was sealed and incubated at 37° C. for 12 hours to effect immobilization.

(2) Prehybridization

The plate in which the heat-denatured nucleic acid was thus immobilized was washed with distilled water and 100 µl of a solution for prehybridization was added to each well. The plate was sealed and incubated at 60° C. for 1.5 hours. The prehybridization solution used had the following composition : 5×SSC (1×SSC=0.15M NaCl, 0.015M sodium citrate), 5×Denhardt's solution (0.02% polyvinylpyrrolidone, 0.02% ficoll, 0.02% BSA), 25 mM sodium phosphate buffer (pH 6.5), 50% formamide, and 0.5 mg/ml yeast transfer RNA.

(3) Hybridization

The prehybridization solution in the plate was discarded and a 100 µl portion of a hybridization solution was added to each well, followed by incubation at 42° C. for 12 hours. The hybridization solution had the following composition : 5×SSC, 1×Denhardt's solution, 25 mM sodium phosphate buffer (pH 6.5), 45% formamide, 0.2 mg/ml yeast transfer RNA, and 2 µg/ml fluorescence-labelled DNA.

The fluorescence-labelled DNA used was obtained in Example 12 by introducing a fluorescent group into M13 single-stranded DNA using Compound-1 to Compound-11. This fluorescence-labelled DNA was used after heat-treating at 75° C. for 10 minutes and quenched on ice for 5 minutes.

(4) Elimination of unreacted fluorescence-labelled DNA

The fluorescence-labelled DNA which did not form hybrid with the heat-denatured DNA immobilized on the plate was eliminated in the following manner.

After removing the hybridization solution in each well, 2×SSC, and 150 µl of 0.1% aqueous solution of sodium dodecylsulfate were added, and the plate was shaken at room temperature for 5 minutes using a plate mixer. The same procedure was repeated two more times. The solution in the wells were discarded, and 300 µl of 2×SSC was added, followed by allowing the plate to stand at room temperature for 5 minutes.

(5) Detection of hybrid nucleic acid

To each well were added 50 mM sodium phosphate buffer (pH 7.0) and 100 µl of 1.5M NaCl, and fluorescence intensity was measured respectively using a fluorescence plate reader (Fluorite 1000: manufactured by Dynatec Co.) to determine the amount to be needed for detection (ng/well) of each compound.

As a filter, the one suitable for the excitation wavelength of the fluorescent substances and the fluorescence wavelength was used, respectively. The results are shown in the following table 1.

TABLE 1

| Compound | Limit of detection (ng/well) |
|---|---|
| 1 | 4.8 |
| 2 | 480 |
| 3 | 480 |
| 4 | 4.8 |
| 5 | 48 |
| 6 | 4.8 |
| 7 | 48 |
| 8 | 48 |
| 9 | 48 |
| 10 | 48 |
| 11 | 480 |

Example 14

Using the fluorescence-labelled DNA of the present invention, another example of hybridization was carried out by a microtiter plate method in the following manner.

(1) Immobilization of nucleic acid on the plate

Serial decimal dilutions of phage DNA (replicative form of M13mp18) linearized with a restriction enzyme (HindIII) was prepared using 2M NaCl so as to give 480 ng–4.8 µg/100 µl. The dilutions were heat-treated at 100° C. for 10 minutes and then quenched on ice for 5 minutes to obtain heat-denatured nucleic acid. The thus obtained heat-denatured nucleic acid in various concentrations was added to each well of the black microtiter plate for luminescence and coloring (Sumitomo bakelite Co.) and the plate was sealed and incubated at 37° C. for 12 hours to effect immobilization.

(2) Prehybridization

The plate in which the heat-denatured nucleic acid was thus immobilized was washed with distilled water and 100 µl of a solution for prehybridization was added to each well. The plate was sealed and incubated at 60° C. for 1.5 hours. The prehybridization solution used had the following composition : 5×SSC, 5×Denhardt's solution, 25 mM sodium phosphate buffer (pH 6.5), 50% formamide, and 0.5 mg/ml yeast transfer RNA.

(3) Hybridization

The prehybridization solution in the plate was discarded and a 100 µl portion of a hybridization solution was added to each well, followed by incubation at 42° C. for 12 hours. The hybridization solution had the following composition : 5×SSC, 1×Denhardt's solution, 25 mM sodium phosphate buffer (pH 6.5), 45% formamide, 0.2 mg/ml yeast transfer RNA, and 2 µg/ml fluorescence-labelled DNA.

The fluorescence-labelled DNA used was obtained in the same manner as in Example 12 by introducing a fluorescent group into M13 single-stranded DNA using a compound represented by the following formula as a fluorescent group-containing carbodiimide compound. This fluorescent group-containing carbodiimide compound represented by the following formula was obtained in the same manner as in Example 2 except for changing the fluorescent group-containing thiourea.

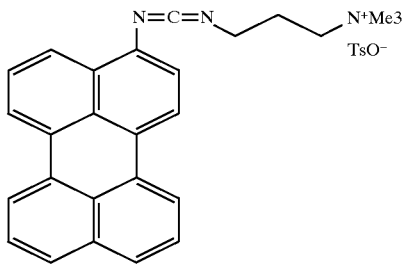

The fluorescence-labelled DNA was used after heat-treating at 75° C. for 10 minutes and quenched on ice for 5 minutes.

(4) Elimination of unreacted fluorescence-labelled DNA

The fluorescence-labelled DNA which did not form hybrid with the heat-denatured DNA immobilized on the plate was eliminated in the following manner.

After removing the hybridization solution in each well, 2×SSC, and 150 μl of 0.1% aqueous solution of sodium dodecylsulfate were added, and the plate was shaken at room temperature for 5 minutes using a plate mixer. The same procedure was repeated two more times. The solution in the wells were discarded, and 300 μl of 2×SSC was added, followed by allowing the plate to stand at room temperature for 5 minutes.

(5) Detection of hybrid nucleic acid

To each well were added 50 mM imidazole nitrate buffer (pH 7.6) and 100 μl of 0.5 mM TPPO acetonitrile, and 25 μl of a 25 mM aqueous solution of hydrogen peroxide was injected into a luminescence plate reader (LUCY1: manufactured by Aloka Co.) to measure emission intensity. As a result, 4.8 μg/well was detected.

Also the detection of nucleic acid was carried out in the same manner as in Example 14 using the M13 single-stranded DNA which was labelled with Compound-7 in the same manner as in Example 12 as fluorescence-labelled DNA. As a result, 480 μg/well was detected.

Example 15

Using the fluorescent group-containing carbodiimide compound of the present invention (Compound-2 synthesized in Example 2) as the label, a protein was detected by the antigen-antibody reaction using a membrane in the following manner.

(1) Labeling of protein with fluorescence

The reaction mixture [anti-rabbit IgG antibody (goat) (Anti-RABBIT IgG (goat), VECTER LABORATORIES) 100 μg; 0.1M borate buffer (pH 9.0); and 0.1M the fluorescent group-containing carbodiimide compound (Compound-2 obtained in Example 2)] was allowed to stand on ice for 10 minutes to label a protein with the fluorescent compound. Then, 10% SDS was added thereto so as to give a concentration of 0.3 based on the total amount and the mixture was centrifuged at 5,000 rpm for 15 minutes using microtube for centrifugation (Ultrafree C3LGC, tradename: Millipore) to remove unreacted carbodiimide compound. Then, 50 μl each of 100 mM sodium phosphate buffer (pH 7.6) and 50 mM NaCl were added to a filter cup to centrifuge at 5,000 rpm for 10 minutes. After repeating the same procedure, the residue was transferred to an Eppendorf tube and 100 mM sodium phosphate buffer (pH 7.6) and 50 mM NaCl were added thereto to give a 0.1M solution. The resulting solution was kept at 4° C.

(2) Immobilization of IgG on the membrane

Ten-fold serial dilutions of rabbit IgG were prepared using buffer A solution in the range from 100 ng/μl to 1 pg/μl. 1 μl of each IgG dilutions was dot blotted on PBDF (polyvinylidene fluoride) membrane (Millipore) and dried at 37° C. for 10 minutes to immobilize IgG on the membrane. Then, the resulting IgG-immobilized membrane was immersed in buffer B solution and allowed to stand for 30 minutes to effect blocking.

Buffer A solution was containing 0.2M NaCl, 0.1M Tris-HCl (pH 7.5), and 0.05% Triton-X-100. Buffer B solution was composed of buffer A solution supplemented with 3% BSA.

(3) Antigen-antibody reaction

The membrane was taken out from the buffer B solution and immersed in the reaction solution with shaking with a shaker at room temperature for 30 minutes. The reaction solution used was composed of 10 ml of buffer A solution and 10 μl of 4 μg/μl fluorescence-labelled anti-rabbit IgG. The fluorescence-labelled anti-rabbit antibody used was obtained by the method described in the (1) above.

(4) Elimination of unreacted fluorescence-labelled anti-rabbit antibody

The unreacted fluorescence-labelled anti-rabbit antibody which did not react with the immobilized antibody was removed by carrying out the washing procedure three times wherein the reacted membrane was immersed in buffer A solution with shaking at room temperature for 5 minutes.

(5) Detection of rabbit IgG by florescence

The membrane wet with buffer A solution was put into a UV box to irradiate ultraviolet light (254 nm). As a result, 1 pg of rabbit IgG was detected.

The Use of the fluorescent group-containing carbodiimide compound of the present invention makes it possible to carry out highly sensitive nucleic acid detection and immunoassay with simple operation.

What is claimed is:

1. A fluorescent group-containing carbodiimide compound represented by the formula (I):

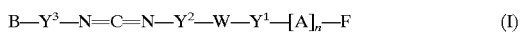

wherein F represents a fluorescent group;

A represents a moiety selected from the group consisting of —CH$_2$—, —NHCO—, —CONH, —O—, —S—, —NR—, wherein R is an alkyl group, —COO—, —OCO—, —NHSO$_2$—, and —SO$_2$NH—;

n is 0 or 1;

W represents a direct bond or a quaternary ammonium group;

Y$^1$, Y$^2$ and Y$^3$ each represents a group having the formula (L):

wherein L is a direct bond or a moiety selected from the group consisting of —NHCO—, —CONH—, —O—, —S—, —NR—, N$^+$RR'—, wherein R' is an alkyl group, —COO—, and —OCO—;

p and q each represents an integer of from 1 to 12; and

B represents a hydrogen atom or a monovalent organic group.

2. The fluorescent group-containing carbodiimide compound as claimed in claim 1, which is a compound represented by the formula (II):

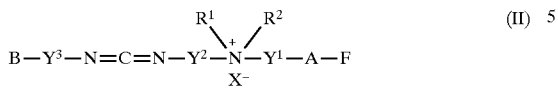
(II)

wherein $R^1$ and $R^2$ each represents a straight-chain or branched, saturated or unsaturated aliphatic hydrocarbon group having from 1 to 6 carbon atoms, a substituted or unsubstituted cycloalkyl group, a substituted or unsubstituted aryl group, a substituted or unsubstituted aralkyl group, or a nitrogen-containing heterocyclic group formed by $R^1$ and $R^2$ which are bound to each other;

$X^-$ represents a halogen atom or a sulfonate ion; and $B, Y^1, Y^2, Y^3$, A and F have the same definition as in the formula (I).

3. The fluorescent group-containing carbodiimide compound as claimed in claim 2, wherein the compound represented by the formula (II) is a compound represented by the formula (III):

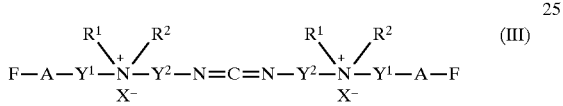
(III)

wherein $R^1, R^2, X^-, Y^1, Y^2$, A and F have the same definition as in the formula (II).

4. The fluorescent group-containing carbodiimide compound as claimed in claim 1, which is a compound represented by the formula (IV):

(IV)

wherein B and $Y^3$ have the same definition as in the formula (I);

F' represents a moiety selected from the group consisting of a coumarin, a pyrene, a perylene, a rhodamine, a dansyl, an oxazole, and a thiazole orange.

5. The fluorescent group-containing carbodiimide compound as claimed in claim 1, which is a compound represented by the formula (V):

(V)

wherein $B, Y^2, Y^3$, A and F have the same definition as in the formula (I).

6. The fluorescent group-containing carbodiimide compound as claimed in claim 1, wherein F in the formula (I) is selected from the fluorescent group represented by the formula (F):

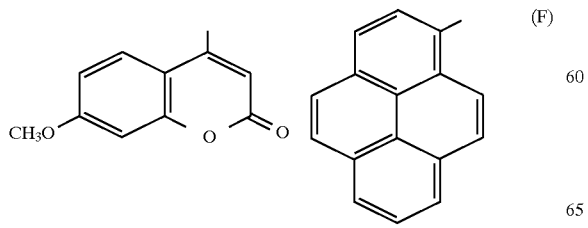
(F)

-continued

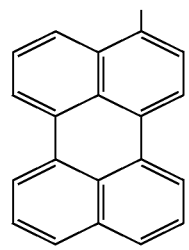

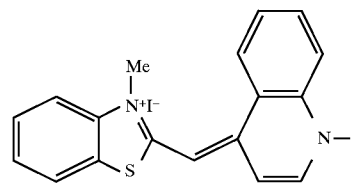

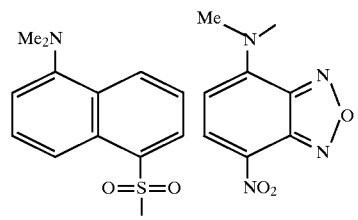

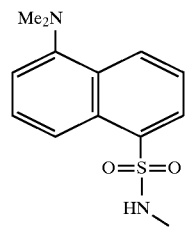

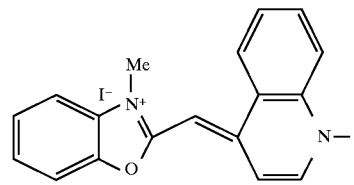

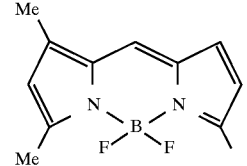

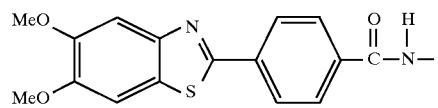

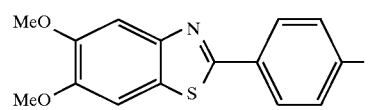

-continued

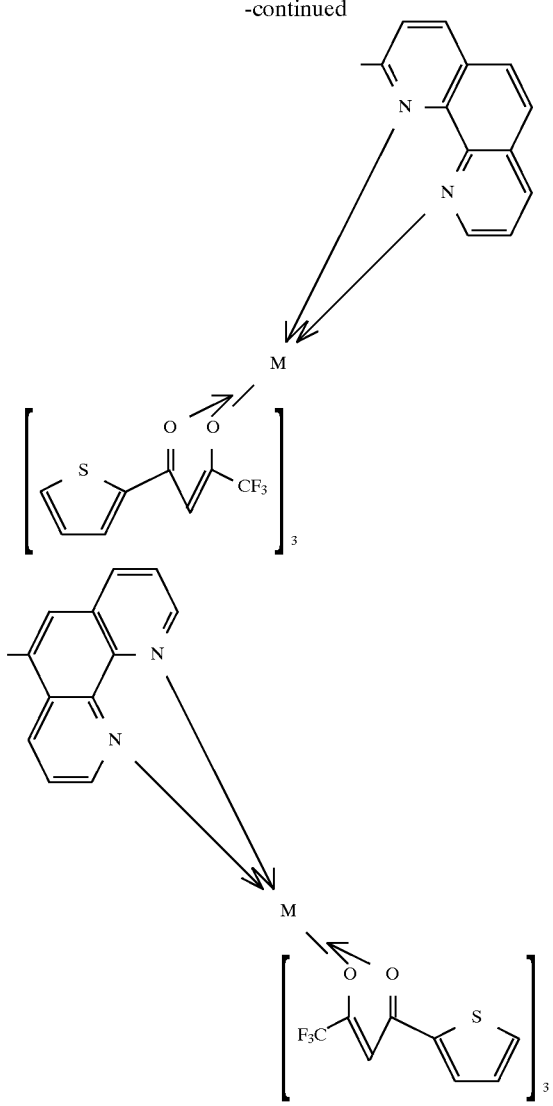

wherein M is $Eu^{3+}$, $Sm^{3+}$, or $Tb^{3+}$.

7. A process for producing the fluorescent group-containing carbodiimide compound as claimed in claim 2, which comprises a step of reacting a carbodiimide group-containing compound represented by the formula (VI):

    (VI)

wherein W' represents substituted or unsubstituted amino group; and B, $Y^3$, and $Y^2$ have the same definition as in the formula (I), with a fluorescent group-containing compound represented by the formula (VII):

    (VII)

wherein F, A, and $Y^1$ have the same definition as in the formula (I); and X is a halogen atom or a sulfonate group.

8. A process for producing the fluorescent group-containing carbodiimide compound as claimed in claim 4 which comprises a step of reacting an amino group-containing fluorescent compound represented by the formula (VIII):

    (VIII)

wherein F' has the same definition as in the formula (IV), with an iso(thio)cyanate compound represented by the formula (IX):

    (IX)

wherein Z represents an oxygen atom or a sulfur atom; and B and $Y^3$ have the same definition as in the formula (IV), to synthesize a (thio)urea compound represented by the formula (X):

    (X)

wherein B, F, Z, and $Y^3$ have the same definition as in the formulae (VIII) and (IX).

9. A process for producing the fluorescent group-containing carbodiimide compound as claimed in claim 5, which comprises a step of reacting an amino group-containing fluorescent compound represented by the formula (XI):

    (XI)

wherein F, A, and $Y^2$ have the same definition as in the formula (V), with an iso(thio)cyanate compound represented by the formula (XII):

    (XII)

wherein Z represents an oxygen atom or a sulfur atom; and B and $Y^3$ have the same definition as in the formula (V), to synthesize a (thio)urea compound represented by the formula (XIII):

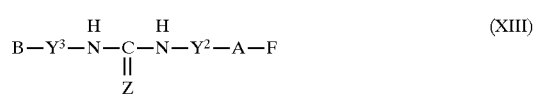    (XIII)

wherein A, B, F, Z, $Y^2$, and $Y^3$ have the same definition as in the formulae (XI) and (XII).

* * * * *